United States Patent
Stahl et al.

(10) Patent No.: US 12,016,366 B2
(45) Date of Patent: *Jun. 25, 2024

(54) NICOTINE POUCH COMPOSITION AND POUCH COMPRISING SUCH

(71) Applicant: PHILIP MORRIS PRODUCTS S.A., Neuchatel (CH)

(72) Inventors: My Ly Lao Stahl, Vejle Ost (DK); Heidi Ziegler Bruun, Vejle Ost (DK); Bruno Provstgaard Nielsen, Vejle Ost (DK); Bine Hare Jakobsen, Ry (DK)

(73) Assignee: PHILIP MORRIS PRODUCTS S.A., Neuchatel (CH)

( * ) Notice: Subject to any disclaimer, the term of this patent is extended or adjusted under 35 U.S.C. 154(b) by 417 days.

This patent is subject to a terminal disclaimer.

(21) Appl. No.: 17/370,641

(22) Filed: Jul. 8, 2021

(65) Prior Publication Data

US 2021/0329962 A1    Oct. 28, 2021

Related U.S. Application Data

(63) Continuation of application No. 16/894,114, filed on Jun. 5, 2020, now Pat. No. 11,096,412.

(30) Foreign Application Priority Data

| Jun. 7, 2019 | (DK) | 201900698 |
| Sep. 30, 2019 | (DK) | 201970610 |
| Sep. 30, 2019 | (DK) | 201970611 |
| Sep. 30, 2019 | (DK) | 201970612 |

(51) Int. Cl.
| *A24B 15/16* | (2020.01) |
| *A24B 13/00* | (2006.01) |
| *A24B 15/24* | (2006.01) |
| *A24B 15/30* | (2006.01) |
| *A24B 15/32* | (2006.01) |
| *A24B 15/38* | (2006.01) |
| *A24B 15/40* | (2006.01) |
| *A24B 15/42* | (2006.01) |
| *A61K 9/00* | (2006.01) |
| *A61K 31/465* | (2006.01) |

(52) U.S. Cl.
CPC ............ *A24B 15/16* (2013.01); *A24B 13/00* (2013.01); *A24B 15/243* (2013.01); *A24B 15/302* (2013.01); *A24B 15/303* (2013.01); *A24B 15/32* (2013.01); *A24B 15/385* (2013.01); *A24B 15/403* (2013.01); *A24B 15/42* (2013.01); *A61K 9/006* (2013.01); *A61K 9/009* (2013.01); *A61K 31/465* (2013.01)

(58) Field of Classification Search
None
See application file for complete search history.

(56) References Cited

U.S. PATENT DOCUMENTS

| 5,167,244 | A | 12/1992 | Kjerstad |
| 8,863,755 | B2 | 10/2014 | Zhuang et al. |
| 9,402,809 | B2 | 8/2016 | Axelsson et al. |
| 11,096,412 | B2 | 8/2021 | Stahl et al. |
| 11,540,557 | B2 * | 1/2023 | Stahl ............... A24B 13/00 |
| 2005/0034738 | A1 | 2/2005 | Whalen |
| 2005/0053665 | A1 | 3/2005 | Ek et al. |
| 2008/0302682 | A1 | 12/2008 | Engstrom et al. |
| 2011/0214681 | A1 | 9/2011 | Axelsson et al. |
| 2012/0247492 | A1 | 10/2012 | Kobal et al. |
| 2013/0108558 | A1 | 5/2013 | Andersen |
| 2013/0152953 | A1 | 6/2013 | Mua et al. |
| 2015/0020818 | A1 | 1/2015 | Gao et al. |
| 2015/0068545 | A1 | 3/2015 | Moldoveanu et al. |
| 2015/0096576 | A1 | 4/2015 | Gao et al. |
| 2015/0272878 | A1 * | 10/2015 | Nilsson ............ A61K 47/38 |
| | | | 514/343 |
| 2016/0000140 | A1 | 1/2016 | Sebastian et al. |
| 2016/0165953 | A1 | 6/2016 | Goode, Jr. |
| 2016/0192703 | A1 | 7/2016 | Sebastian et al. |
| 2017/0318858 | A1 | 11/2017 | Hodin et al. |
| 2018/0271139 | A1 | 9/2018 | Aspgren et al. |
| 2019/0037909 | A1 | 2/2019 | Greenbaum et al. |
| 2020/0138089 | A1 * | 5/2020 | Duignan ............ A24F 23/02 |
| 2020/0297024 | A1 | 9/2020 | Bodin |

FOREIGN PATENT DOCUMENTS

| CA | 2 949 579 A1 | 11/2015 |
| CN | 102481257 A | 5/2012 |
| CN | 106413697 A | 2/2017 |
| CN | 107319629 A | 11/2017 |

(Continued)

OTHER PUBLICATIONS

Definition of "complex", IUPAC. Compendium of Chemical Terminology, 2nd ed. (the "Gold Book"), 1997, [online], [retrieved on Jun. 24, 2014], Retrieved from the Internet: <URL: http://goldbook.iupac.org (2006-)>. (Year: 1997).*
Additional Search Report from Danish Patent and Trademark Office for Application No. PA 2019 70610 dated Jul. 30, 2020 (2 pages).
Additional Search Report from Danish Patent and Trademark Office for Application No. PA 2019 70612 dated Aug. 4, 2020 (2 pages).
Search Report from Danish Patent and Trademark Office for Application No. PA 2019 00698 dated Dec. 3, 2019 (1 page).
Search Report from Danish Patent and Trademark Office for Application No. PA 2019 70610 dated Feb. 5, 2020 (2 pages).
Search Report from Danish Patent and Trademark Office for Application No. PA 2019 70611 dated Feb. 5, 2020 (2 pages).
Search Report from Danish Patent and Trademark Office for Application No. PA2019 70612 dated Feb. 3, 2020 (2 pages).

(Continued)

*Primary Examiner* — Dennis R Cordray
(74) *Attorney, Agent, or Firm* — Oblon, McClelland, Maier & Neustadt, L.L.P.

(57) ABSTRACT

A nicotine pouch composition is disclosed, the pouch composition comprising free-base nicotine and having a water content of at least 15% by weight of said pouch composition. Furthermore, an oral nicotine pouch product comprising the pouch composition and a method for manufacturing the oral nicotine pouch product is disclosed.

29 Claims, No Drawings

(56) References Cited

FOREIGN PATENT DOCUMENTS

| | | | |
|---|---|---|---|
| EP | 2692254 A1 | 2/2014 | |
| EP | 3087852 A1 | 11/2016 | |
| EP | 3491940 A1 | 6/2019 | |
| GB | 673587 A | 6/1952 | |
| NO | 20170683 A1 | 10/2018 | |
| RU | 2 283 111 C2 | 9/2006 | |
| RU | 2 457 822 C2 | 8/2012 | |
| RU | 2 689 882 C2 | 5/2019 | |
| SE | 1950119 A1 | 9/2020 | |
| WO | 2007084587 A2 | 7/2007 | |
| WO | 2007104573 A2 | 9/2007 | |
| WO | 2008056135 A2 | 5/2008 | |
| WO | 2009010881 A2 | 1/2009 | |
| WO | 2010121619 A1 | 10/2010 | |
| WO | WO 2011/150959 A1 | 12/2011 | |
| WO | WO 2011/150960 A1 | 12/2011 | |
| WO | 2012134380 A1 | 10/2012 | |
| WO | 2013090366 A2 | 6/2013 | |
| WO | 2013152918 A1 | 10/2013 | |
| WO | WO 2013/147687 A1 | 10/2013 | |
| WO | 2015052282 A1 | 4/2015 | |
| WO | 2015067372 A1 | 5/2015 | |
| WO | 2015193379 A1 | 12/2015 | |
| WO | 2016083463 A1 | 6/2016 | |
| WO | 2017153718 A1 | 9/2017 | |
| WO | 2018011470 A1 | 1/2018 | |
| WO | 2018126262 A2 | 7/2018 | |
| WO | 2018147454 | 11/2018 | |
| WO | 2018197454 A1 | 11/2018 | |
| WO | 2018233795 A1 | 12/2018 | |
| WO | 2019115778 A1 | 6/2019 | |
| WO | 2020157280 A1 | 8/2020 | |

OTHER PUBLICATIONS

International Search Report Application No. PCT/DK2020/050159; dated Aug. 12, 2020; 3 pages.
International Search Report Application No. PCT/DK2020/050160; dated Oct. 1, 2020; 3 pages.
International Search Report Application No. PCT/DK2020/050162; dated Oct. 2, 2020; 4 pages.
International Search Report Application No. PCT/DK2020/050163; dated Oct. 7, 2020; 4 pages.
Seidenberg, Andrew B., Olalekan A. Ayo-Yusuf, and Vaughan W. Rees. Characteristics of American Snu▲ and Swedish Snus Products for Sale in Massachusetts, USA. Nicotine and Tobacco Research 20.2 (2018): 262-266.
Wikipedia, "Sugar alcohol"; https://en.wikipedia.org/wiki/Sugar_alcohol; downloaded from Internet on Sep. 27, 2017.
Combined Chinese Office Action and Search Report dated Jun. 30, 2023 in Chinese Patent Application No. 202080041508.X (with English Translation), 15 pages.
Material Safety Data Sheet, Spectrum, 2010, Retrieved from the Internet: URL:https://protect-us.mimecast.com/s/W04a-CORXYkhGVriBlwtF_Gy?domain=images-na.ssl-images-amazon.com, 7 pages.
BGP Healthcare Private Limited Data Sheet, 2010, Retrieved from the Internet: URL: https://www.bgpgroup.niz/wpcontent.themes/avada/pdf/09%20MSDS%20NICOTINE%20POLACRILEX%2020.pdf, 8 pages.
"Shelf life of medicinal products, OFS.1.1.0009.15", Ministry of Health of the Russian Federation, XIII Edition, Moscow, 2015, 16 pages.
Khoruzhaya et al., "Biopharmacy—scientific direction in development and improvement of drugs", Ministry of Education and Science of the Russian Federation State educational institution higher professional education, Siberian State Medical University, Federal Agency for Health and Social Development, 2006, 2 pages.
Tikhonov et al., "Biopharmacy: Textbook for students of pharmaceutical universities and faculties", Ministry of Health Ukraine Ainy National Pharmaceutical University, 2003, pp. 28-30.
Combined Russian Office Action and Search Report dated Nov. 14, 2023 in Russian Patent Application No. 2021139809 (with English translation), 37 pages.

\* cited by examiner

NICOTINE POUCH COMPOSITION AND POUCH COMPRISING SUCH

FIELD OF THE INVENTION

The present invention relates to a nicotine pouch composition having a water content of at least 15% by weight, an oral nicotine pouch product comprising the pouch composition, and methods for producing such pouch.

BACKGROUND OF THE INVENTION

Delivery of nicotine by smoking has many well-known drawbacks, in particular health related problems, such as inclusion of carcinogenic substances.

However, tobacco substitutes also suffer from disadvantages, such as inadequate relief of cravings for the recovering smoker.

It is an object of the present invention to provide a nicotine containing pouch, e.g. as a tobacco substitute, which may solve the above problems.

SUMMARY OF THE INVENTION

The invention relates to a nicotine pouch composition comprising free-base nicotine and having a water content of at least 15% by weight of said pouch composition.

An advantage of the invention may be that a more desirable mouthfeel may be obtained for the same amount of nicotine compared to pouch compositions with lower moisture content. By applying free-base nicotine, the recognizable burning sensation may be obtained, thereby better emulating tobacco containing products.

A further advantage of the invention may be that a relatively fast release of nicotine may be obtained, e.g. by avoiding any delays associated with release of ionized nicotine bound to a carrier. The fast release of nicotine advantageously provides for a fast relief of nicotine craving for the users. Also, the high water content further facilitates fast release of nicotine as the delay typically associated with moisture attraction to a pouch may be more or less avoided.

By providing the nicotine as free-base nicotine, a relatively high pH in the resulting saliva of a user may be obtained due to the nicotine being provided as in its free base form compared to e.g. nicotine bitartrate. Thereby, either a higher pH value may be obtained or a reduced amount of pH regulating agent to achieve the same pH value. A higher pH value promotes nicotine absorption over the oral mucosa.

Also, an advantage of the invention may be that a relatively fast release and resulting nicotine craving relief may be obtained as a result a combination of using nicotine in a non-ionized free-base form and having a relatively high water-content. Thereby, the pouch product may provide a relatively fast release of nicotine into saliva and a subsequent fast uptake of nicotine over the oral mucous membrane due to the high oral pH thereby obtaining a fast effect for the user.

Moreover, the use of free-base nicotine advantageously provides for a pouch product giving a desired texture and mouthfeel and provides nicotine craving relief. While any degradation of nicotine due to the presence of water may to some extend lower the amount of available nicotine for the user, by providing the nicotine as free-base nicotine a higher pH value may be obtained, whereby any decrease in the amount of nicotine is compensated for both in terms of mouthfeel and since the higher pH facilitates a more effective update of nicotine. At the same time, the high pH may increase shelf life due to inhibition of undesirable microbiological growths. Also, the water content and the free-base form of nicotine synergistically facilitates a fast uptake of nicotine.

The pouch composition may also provide fora desirable mouthfeel such as a soft and sticky texture. The desirable texture and mouthfeel may be obtained while still being able to store manufactured pouches together in abutment e.g. in cans etc. without sticking too much together to result in ruptures of the pouches when being removed. The desirable mouthfeel may in some embodiments also comprise a tingling or burning sensation reminiscent of tobacco pouches, but without many the of undesirable effects associated therewith e.g. in view of health, discoloring etc.

A further advantage of the invention may be that an obtained nicotine pouch product comprising the pouch composition has a relatively low tendency to release dusty material through the permeable pouch wall, e.g. in a packaging such as a can. This is advantageous both in the sense that no or only very little of the expensive nicotine is wasted but also in the sense that any such loose material in cans is typically considered very unattractive by users.

The present inventors found that the pouch composition of the invention could provide surprisingly acceptable stability of free-base nicotine in the presence of a high water-content of at least 15% by weight of water. In more detail, pouches comprising the pouch composition provided nicotine craving relief also after storage.

Obtaining a relatively fast release of nicotine and an effective uptake is desirable as this ensures a fast effect for the user. Moreover, this may be obtained with a decreased need for enhancers such as pH regulating agent, due to the use of free-base nicotine, whereby production may be simplified.

In an advantageous embodiment of the invention, the free-base nicotine comprises free-base nicotine mixed with ion exchange resin and/or with a water-soluble composition such as sugar alcohol or water-soluble fiber.

An advantage of the above embodiment may be that a relatively fast release of nicotine may be obtained, compared to e.g. use of nicotine-ion exchange resin complex such as nicotine polacrilex resin.

In an embodiment of the invention, the free-base nicotine consists of free-base nicotine mixed with an ion exchange resin and/or with a water-soluble composition such as sugar alcohol or water-soluble fiber.

In an advantageous embodiment of the invention, the free-base nicotine comprises free-base nicotine mixed with ion exchange resin.

One advantage of the above embodiment may be providing sustained release of nicotine compared to e.g. free-base nicotine mixed with water soluble compositions such as e.g. sugar alcohols. At the same time, the release of nicotine is not too slow to give the user the craving relief desired. Thus, compared to e.g. use of nicotine-ion exchange resin complex, a relatively fast release may be obtained.

Another advantage of the above embodiment may be that it provides a relatively cost-effective solution.

At the same time, a relatively high pH value may be obtained during use compared to the amounts of pH regulating agents used.

In an embodiment the free-base nicotine consists of free-base nicotine mixed with ion exchange resin.

In an advantageous embodiment of the invention, the free-base nicotine comprises free-base nicotine mixed with polacrilex resin.

In an embodiment the free-base nicotine consists of free-base nicotine mixed with polacrilex resin.

In an embodiment of the invention, the free-base nicotine comprises nicotine mixed with ion exchange resin, such as polacrilex resin, the nicotine pouch composition further comprises nicotine bound to an ion exchange resin, i.e. a nicotine ion exchange resin complex. Thus, the nicotine may be nicotine mixed with polacrilex resin, where some nicotine is bound to the ion exchange resin, whereas some nicotine remains unbound as free-base nicotine.

In an advantageous embodiment of the invention the free-base nicotine comprises free-base nicotine mixed with ion exchange resin in a weight ratio between the free-base nicotine and the ion exchange resin of 0.1 to 2.0, preferably from 0.5 to 2.0, and most preferred about 0.67 to 1.0.

In an advantageous embodiment of the invention the free-base nicotine comprises free-base nicotine mixed with ion exchange resin in a weight ratio between the free-base nicotine and the ion exchange resin of 1:1 to about 1:10, preferably from 1:2 to 1:6, and most preferred about 1:4-1:5.

Here, a weight ratio refers to the ratio of the mass of the first component divided by the mass of the second component. The term mixing ratio may also be used.

Thus, in the above embodiment, the free-base nicotine comprises free-base nicotine mixed with ion exchange resin in a weight ratio between the free-base nicotine and the ion exchange resin of 0.1 to about 1, preferably from 0.17 to 0.5, and most preferred about 0.2-0.25.

In an advantageous embodiment of the invention, the free-base nicotine comprises free-base nicotine mixed with water-soluble composition such as sugar alcohol or water-soluble fiber.

An advantage of the above embodiment may be that a relatively fast release of nicotine may be obtained, compared to e.g. use of nicotine-ion exchange resin complex such as nicotine polacrilex resin.

At the same time, a relatively high pH value may be obtained during use compared to the amounts of pH regulating agents used.

In an embodiment the free-base nicotine consists of free-base nicotine mixed with a water-soluble composition, such as sugar alcohol or water-soluble fiber.

In an advantageous embodiment of the invention, the pouch composition comprises water-soluble composition, such as sugar alcohol or water-soluble fiber, in an amount of 1-80% by weight of the pouch composition, such as 5-70% by weight of the pouch composition, such as 10-60% by weight of the pouch composition.

When the free-base nicotine is mixed with the water-soluble composition, such as sugar alcohol or water-soluble fiber, the amounts of water-soluble composition, such as sugar alcohol or water-soluble fiber, may typically be at least 5% by weight of the pouch composition, such as at least 10% by weight of the pouch composition. When using a larger concentration of free-base nicotine in the pouch composition, it may be advantageous to increase the amount of the water-soluble composition, such as sugar alcohol or water-soluble fiber, used in the mixing with the free-base nicotine. Similarly, for lower amounts of free-base nicotine, the need for the water-soluble composition, such as sugar alcohol or water-soluble fiber, may be decreased. Additional the water-soluble composition, particularly sugar alcohol, may be used e.g. as a bulk sweetener, filler etc.

In an advantageous embodiment of the invention, the free-base nicotine comprises free-base nicotine mixed with sugar alcohol.

In an embodiment the free-base nicotine consists of free-base nicotine mixed with sugar alcohol.

In an advantageous embodiment of the invention, said sugar alcohol is selected from the group consisting of sorbitol, erythritol, xylitol, lactitol, maltitol, mannitol, hydrogenated starch hydrolyzates, isomalt, or any combination thereof.

In an embodiment of the invention, the sugar alcohol is provided as a direct compressible (DC) forms of the sugar alcohol. An advantage of this embodiment may be that increase flowability may be achieved.

In an advantageous embodiment of the invention, the free-base nicotine comprises free-base nicotine mixed with water-soluble fiber.

In an embodiment the free-base nicotine consists of free-base nicotine mixed with water-soluble fiber.

In an advantageous embodiment of the invention, said water-soluble fiber is selected from the list of inulin, polydextrose including refined polydextrose, dextrin, maltodextrin, and mixtures thereof.

In an advantageous embodiment of the invention, the free-base nicotine mixed with ion exchange resin further comprises water.

Thus, in the above embodiment, the mixture of nicotine with ion exchange resin further comprises water. This mixture comprising water is then added to the further ingredients, which typically may comprise further water to obtain the water content of at least 15% by weight of the pouch composition.

In an advantageous embodiment of the invention, the pouch composition comprises a combination of free-base nicotine mixed with a first compositions and free-base nicotine mixed with a second, different composition.

It is understood that the first and second compositions are different. One example is free-base nicotine mixed with ion exchange resin combined with free-base nicotine mixed with a water-soluble composition, such as sugar alcohol or water-soluble fiber. Another example is a combination of free-base nicotine mixed with sugar alcohol combined with free-base nicotine mixed with water-soluble fiber. Yet another example is a combination of free-base nicotine mixed with one type of ion exchange resin combined with free-base nicotine mixed with another type of ion exchange resin, or a combination of free-base nicotine mixed with one type of water-soluble fiber combined with free-base nicotine mixed with another type of water-soluble fiber, or a combination of free-base nicotine mixed with one type of sugar alcohol combined with free-base nicotine mixed with another type of sugar alcohol.

In an advantageous embodiment of the invention, the free base nicotine comprises a combination of free-base nicotine mixed with a water-soluble composition and free-base nicotine mixed with a water-insoluble composition.

An advantage of the above embodiment may be that a release profile of nicotine may be obtained which both comprises a fast release component and a sustained release component, which may be desirable for users of the nicotine pouch products.

Examples of usable water-insoluble compositions may e.g. include water-insoluble fibers such as plant fibers, bran fibers, and cellulose fibers, hereunder microcrystalline cellulose (MCC).

In an advantageous embodiment of the invention, the free-base nicotine comprises a combination of free-base nicotine mixed with ion exchange resin and free-base nicotine mixed with a water-soluble composition.

An advantage of the above embodiment may be that a release profile of nicotine may be obtained which both comprises a fast release component and a sustained release component, which may be desirable for users of the nicotine pouch products.

In an advantageous embodiment of the invention, the free-base nicotine is granulated with the water-soluble composition or ion exchange resin.

In an advantageous embodiment of the invention, the pouch composition further comprises a pH-regulating agent, such as a basic pH-regulating agent, such as a basic buffering agent.

An advantage of the above embodiment may be that a more effective uptake of nicotine may be obtained.

Another advantage of the above embodiment may be that a desirable mouthfeel may be obtained during use.

In an embodiment of the invention, the pouch composition further comprises a combination of at least two pH-regulating agents, such as a combination of at least two basic pH-regulating agents, such as a combination of at least two basic buffering agents, such as a basic buffer pair.

While lower amounts of pH regulating agent may be applicable in embodiments, e.g. by avoiding the use of nicotine salts, such as nicotine bitartrate, it may still be desirable to further increase the pH by adding pH regulating agent.

In an embodiment of the invention, the pouch composition comprises pH regulating agent, e.g. in an amount of 0.01 and 15% by weight of the pouch composition.

In an advantageous embodiment of the invention, the pouch composition comprises pH regulating agent in an amount between 0.01 and 15% by weight of the pouch composition, such as between 0.5 and 10% by weight of the pouch composition, such as between 1 and 10% by weight of the pouch composition, such as between 5 and 10% by weight of the pouch composition.

In an advantageous embodiment of the invention, the pouch composition is adapted to give a pH of at least 8.0.

In an embodiment of the invention, the pouch composition is adapted to give a pH of at least 8.0, such as a pH of at least 9.0, when 2.0 gram of pouch composition is added to 20 mL of 0.02 M potassium dihydrogen phosphate-buffer (pH adjusted to 7.4).

In an embodiment of the invention, the pouch composition is adapted to give a pH of at least 8.0 during use after being placed in the oral cavity.

An advantage of the above embodiment may be that a relatively effective uptake of nicotine is facilitated due to the high pH value obtained.

A further advantage of the above embodiment may be that the need for preservative may be decreased or even eliminated and that low amounts of such preservatives may be used if not absent.

Also, the high pH value obtained may advantageously provide for a tingling sensation in the mouth which may be perceived as a desirable mouthfeel, e.g. due to resemblance with tobacco-based pouch products.

In an advantageous embodiment of the invention, the pH regulating agent is selected from the group consisting of Acetic acid, Adipic acid, Citric acid, Fumaric acid, Glucono-δ-lactone, Gluconic acid, Lactic acid, Malic acid, Maleic acid, Tartaric acid, Succinic acid, Propionic acid, Ascorbic acid, Phosphoric acid, Sodium orthophosphate, Potassium orthophosphate, Calcium orthophosphate, Sodium diphosphate, Potassium diphosphate, Calcium diphosphate, Pentasodium triphosphate, Pentapotassium triphosphate, Sodium polyphosphate, Potassium polyphosphate, Carbonic acid, Sodium carbonate, Sodium bicarbonate, Potassium carbonate, Calcium carbonate, Magnesium carbonate, Magnesium oxide, or any combination thereof.

In an advantageous embodiment of the invention, the pH regulating agent is a basic pH regulating agent, such as a basic buffering agent and/or such as Sodium carbonate, Sodium bicarbonate, Potassium carbonate, Potassium bicarbonate, Magnesium carbonate, or any combination thereof.

In an advantageous embodiment of the invention, the pouch composition further comprises a humectant.

The humectant may attract and retain water in the oral cavity during use. However, the humectant may additionally moderate the release of nicotine, e.g. to facilitate a sustained release of nicotine.

In an advantageous embodiment of the invention, the pouch composition further comprises humectant in an amount of 0.5 to 10% by weight of the pouch composition, such as 0.5 to 5% by weight of the pouch composition, such as 1-3% by weight of the pouch composition.

In an advantageous embodiment of the invention, the humectant comprises one or more from the list consisting of glycerol, propylene glycol, alginate, modified starch, hydroxypropyl cellulose, triacetin, polyethylene glycol (PEG), pectin, and xanthan gum.

In an advantageous embodiment of the invention, the pouch composition further comprises alginate.

In an embodiment of the invention, the pouch composition further comprises glycerol.

In an embodiment of the invention, the pouch composition further comprises modified starch.

In an embodiment of the invention, the pouch composition further comprises hydroxypropyl cellulose (HPC).

An advantage of the above embodiment may be that pouch composition during use provides a desirable soft texture. The alginate may e.g. be provided as a humectant, and thus attract and retain water in the oral cavity during use. However, the alginate may additionally moderate the release of nicotine, e.g. to facilitate a sustained release of nicotine.

In an advantageous embodiment of the invention, the pouch composition further comprises alginate in an amount of 0.5 to 5% by weight of the pouch composition, such as 1-3% by weight of the pouch composition.

In an advantageous embodiment of the invention, the pouch composition further comprises xanthan gum.

An advantage of the above embodiment may be that pouch composition during use provides a desirable soft texture. The xanthan gum may e.g. be provided as a humectant, and thus attract and retain water in the oral cavity during use.

In an advantageous embodiment of the invention, the pouch composition further comprises silicon dioxide.

An advantage of the above embodiment may be that an improved flowability of the pouch composition is obtained. Thus, the silicon dioxide may be provided as a glidant. Alternative glidants may also be used in embodiments where glidants are used.

In an embodiment of the invention, the pouch composition further comprises silicon dioxide in an amount of 0.5 to 5% by weight of the pouch composition, such as 1-3% by weight of the pouch composition.

In an advantageous embodiment of the invention, the pouch composition comprises flavor, e.g. in an amount of 0.01 and 20% by weight of the pouch composition, such as in an amount of 0.01 and 15% by weight of the pouch composition.

In an embodiment of the invention, the pouch composition comprises flavor in an amount between 0.01 and 15% by weight of the pouch composition, such as between 0.1 and 15% by weight of the pouch composition, such as between 1 and 10% by weight of the pouch composition, such as between 3 and 10% by weight of the pouch composition.

In an advantageous embodiment of the invention, the flavor comprises liquid flavor.

The properties of the water-insoluble component may influence the release of the flavor from the pouch composition and thereby possible influence the perception of flavor by the user.

In an embodiment of the invention the water-insoluble fiber may cause a higher or lower perception of flavor to the user.

In an embodiment of the invention, the pouch composition comprises flavor in an amount of no more than 10% by weight of the pouch composition, such as no more than 8% by weight of the pouch composition, such as no more than 5% by weight of the pouch composition.

In an embodiment of the invention, the pouch composition comprises flavor in an amount of 0.01-10% by weight of the pouch composition, such as 0.01-8% by weight of the pouch composition, such as 0.01-5% by weight of the pouch composition.

In an advantageous embodiment of the invention, the pouch composition comprises water-insoluble fibers selected from pea fibers, powdered cellulose, and combinations thereof, and flavor in an amount of no more than 10% by weight of the pouch composition.

Cellulose prepared by processing alpha-cellulose obtained as a pulp from strains of fibrous plant materials may e.g. be obtained from wood pulp.

In an embodiment of the invention, the pouch composition comprises water-insoluble fibers selected from pea fibers and powdered cellulose, or a combination thereof, and flavor in an amount of 0.01-10% by weight of the pouch composition.

In an advantageous embodiment of the invention, the pouch composition is substantially homogenous.

For example, when mixing at least 90% by weight of the total amount of dry ingredients before adding nicotine followed by water, such as before adding nicotine followed by water and liquid flavors, if any, a more homogeneous pouch composition may be obtained, having an even distribution of nicotine.

In an advantageous embodiment of the invention, the content of nicotine between a series of at least 10 oral pouches comprising said pouch composition holds a relative standard deviation (RSD) below 10%, preferably below 8%, more preferably at most 6%, even more preferably at most 4%, most preferably at most 2%.

In an embodiment of the invention, the content of the nicotine between a series of at least 10 oral pouches comprising said pouch composition holds a relative standard deviation (RSD) of 0.1-10%, preferably 0.1-8%, more preferably 0.1-6%, even more preferably 0.1-4%, and most preferably 0.1-2%.

Homogeneity of a pouch composition may be assessed by evaluating the distribution between individual pouches of single components of the composition.

For example, the standard deviation of the nicotine content can be measured as described in example 3J. content, i.e. nicotine content uniformity (CU), relates to the homogeneity of the pouch composition. Pouches prepared from the same pouch composition and having a low standard deviation on the nicotine content will have a high pouch composition homogeneity, whereas pouches prepared from the same pouch composition and having a high standard deviation on the nicotine content will have a low pouch composition homogeneity.

In an advantageous embodiment of the invention, the pouch composition is obtained by mixing dry ingredients before adding nicotine, water and liquid flavors, if any.

An advantage of the above embodiment may be that an improved homogeneity of the pouch composition may be obtained.

In an advantageous embodiment of the invention, the pouch composition is obtained by mixing at least 90% by weight of the total amount of dry ingredients before adding water, such as before adding water and liquid flavors, if any.

An advantage of the above embodiment may be that an improved homogeneity of the pouch composition may be obtained.

In an advantageous embodiment of the invention, the pouch composition further comprises an amount of a water-insoluble composition.

An advantage of the above embodiment may be that a residue is left even after use of a nicotine pouch comprising the pouch composition. This may lead to a pleasant perception for users of the nicotine pouch, e.g. due to similarity with tobacco containing products.

In an advantageous embodiment of the invention, the water-insoluble composition comprises at least one selected from dibasic calcium phosphate, calcium carbonate, mono-diglyceride powder, hydrogenated vegetable oil, and combinations thereof.

In an advantageous embodiment of the invention, said amount of said water-insoluble composition is between 5 and 50% by weight of the pouch composition, such as between 10 and 30% by weight of the pouch composition.

In an advantageous embodiment of the invention, the water-insoluble composition comprises or consists of water-insoluble fiber, such as a water-insoluble plant fiber, such as wheat fibers, oat fibers, pea fibers, rice fiber, maize fibers, oat fibers, tomato fibers, barley fibers, rye fibers, sugar beet fibers, buckwheat fibers, potato fibers, cellulose fibers, apple fibers, cocoa fibers, cellulose fiber, powdered cellulose, bamboo fibers, bran fibers or combinations thereof.

Powdered cellulose within the scope of the invention is understood to be cellulose prepared by processing alpha-cellulose obtained as a pulp from strains of fibrous plant materials, such as wood pulp.

In an embodiment of the invention, the water-soluble fiber comprises or consists of cereal fibers.

In an embodiment of the invention, the water-soluble fiber comprises or consists of fruit and/or vegetable fibers.

In an advantageous embodiment of the invention, the water-insoluble composition comprises or consists of water-insoluble fiber, such as a water-insoluble plant fiber, such as wheat fibers, oat fibers, pea fibers, powdered cellulose, or combinations thereof.

In an advantageous embodiment of the invention, the water-insoluble composition comprises or consists of water-insoluble fiber, such as a water-insoluble plant fiber, such as wheat fibers, oat fibers, pea fibers, or combinations thereof.

In an advantageous embodiment of the invention, the water-insoluble composition comprises or consists of water-insoluble fiber, such as a water-insoluble plant fiber, such as wheat fibers, oat fibers, or combinations thereof.

Non-limiting examples of usable plant fibers include Vitacel WF 600, Vitacel HF 600, Vitacel P95, Vitacel WF 200, Vitacel LOO, Vitacel Erbsenfaser EF 150, Vitacel bamboo fiberbaf 90, Vitacel HF 600, Vitacel Cellulose L700G, Vitacel PF200, Vitacel potatofiber KF200, Vitacel bamboo fiberhaf BAF40, Vitacel Haferfaser/oat fiber HF-401-30 US.

Non-limiting examples of usable powdered cellulose include Vitacel L 00, Vitacel Cellulose L700G, Vitacel LC1000, Vitacel L600-20, Vitacel L600 etc.

In an embodiment, the powdered cellulose is chemically unmodified. Thus, powdered cellulose may be chemically unmodified cellulose fibers, which do not include e.g. microcrystalline cellulose (MCC).

In an advantageous embodiment of the invention, the water-insoluble fiber has a water binding capacity of at least 200%, such as at least 300%, such as at least 400%.

An advantage of the above embodiment may be that the high water-binding capacity enables pouch compositions having a high water-content.

Furthermore, the pouches having a high water-content where found to have a desirable texture and mouthfeel may while still being able to store manufactured pouches together in abutment e.g. in cans etc. without sticking too much together to result in ruptures of the pouches when being removed.

In an embodiment of the invention, the water-insoluble fiber has a water binding capacity of 200% to 1500%, such as 300 to 1300%, such as 200 to 800%, such as 300 to 800%, such as 400 to 600%.

In an embodiment of the invention, the water-insoluble fiber has a water binding capacity of 200 to 1500%, such as 300 to 1300%, such as 300 to 900%, such as 300 to 700%, such as 400 to 700%.

In an embodiment of the invention, the water-insoluble fiber has a water binding capacity of 200 to 1500%, such as 400 to 1500%, such as 500 to 1500%, such as 500 to 1200%, such as 500 to 1000%.

In an embodiment of the invention, the water-insoluble fiber has a swelling capacity of at least 5.0 mL/g, such as 5.0-20 mL/g.

An advantage of the above embodiment is that the amount of water-insoluble fiber can be reduced without compromising the mouthfeel during use. If an amount of water-insoluble fiber is substituted for a water-soluble component, the swelling of the water-insoluble fiber will during use counteract the dissolution of the water-soluble component, thereby the user will not experience any decrease in pouch content during use.

In an advantageous embodiment of the invention, the water-insoluble composition comprises or consists of water-insoluble fiber in an amount between 5 and 50% by weight of the pouch composition and a water content of 15 to 70% by weight of said pouch composition.

In an advantageous embodiment of the invention, the water-insoluble fibers are selected from pea fibers, powdered cellulose, and combinations thereof, and wherein the pouch composition comprises flavor in an amount of no more than 10% by weight of the pouch composition.

The pouch composition of the above embodiment may also provide for a desirable mouthfeel such as a soft and sticky texture. The desirable texture and mouthfeel may be obtained while still being able to store manufactured pouches together in abutment e.g. in cans etc. without sticking too much together to result in ruptures of the pouches when being removed. The desirable mouthfeel may in some embodiments also comprise a tingling sensation reminiscent of tobacco pouches, but without many the of undesirable effects associated therewith e.g. in view of health, discoloring etc.

In an embodiment of the invention, the pouch composition comprises water-insoluble fiber in an amount of 5-50% by weight of the pouch composition, such as 10-40% by weight of the pouch composition.

In an advantageous embodiment of the invention, the pouch composition has a water content of at least 20% by weight of said pouch composition, such as at least 25% by weight of said pouch composition, such as at least 30% by weight of said pouch composition, such as at least 40% by weight of said pouch composition.

The water may be added as a separate component of be fully or partly mixed into other components, such as fibers. E.g. when adding free-base nicotine as a mixture of free-base nicotine with ion exchange resin and water, a significant amount of water of the final pouch composition may come from the free-base nicotine-ion exchange resin-water pre-mixture. For example, if the final amount pouch composition comprises 5% water from free-base nicotine-ion exchange resin-water pre-mixture, then up to one third of the water in the pouch composition derives from the free-base nicotine-ion exchange resin-water pre-mixture.

In an advantageous embodiment of the invention, the pouch composition has a water content of 15 to 70% by weight of said pouch composition, such as 15 to 65% by weight of said pouch composition, such as 15 to 50% by weight of said pouch composition, such as 25 to 50% by weight of said pouch composition, such as 30 to 40% by weight of said pouch composition.

In an advantageous embodiment of the invention, the pouch composition has a water content of 15 to 70% by weight of said pouch composition, such as 15 to 50% by weight of said pouch composition, such as 15 to 40% by weight of said pouch composition, such as 15 to 30% by weight of said pouch composition, such as 15 to 25% by weight of said pouch composition.

In an advantageous embodiment of the invention, the composition has a bulk density of at most 0.8 g/cm3, such as has a bulk density of at most 0.7 g/cm3, such as at most 0.6 g/cm3, such as at most 0.5 g/cm3.

The inventive use of a composition having a relatively low bulk density, will provide not only a good mouthfeel, but also an effective release from the pouch, due to the fact that a relatively low bulk density promotes effective salivation and thereby release of water-soluble ingredients of the composition. It is in particular noted that the low bulk density, in combination with the claimed water content, is attractive when improved user perception is desired.

At the same time, a low density advantageously lowers the need for raw materials and thereby decreases production costs.

An advantage of the above embodiment may be that a low-density composition may be obtained. Unexpectedly, the combination of water and sugar alcohols did not lead to a very dense, compact and un-processable pouch composition but allowed a relatively light and low-density composition.

In an advantageous embodiment of the invention, the composition has a bulk density between 0.2 g/cm3 and 0.8 g/cm3, such as between 0.3 g/cm3 and 0.7 g/cm3, such as between 0.3 g/cm3 and 0.6 g/cm3, such as between 0.4 and 0.5 g/cm3.

In an embodiment of the invention, the composition has a bulk density between 0.2 g/cm3 and 0.8 g/cm3, such as between 0.2 g/cm3 and 0.7 g/cm3, such as between 0.2 g/cm3 and 0.6 g/cm3, such as between 0.2 and 0.5 g/cm3.

In an embodiment of the invention, the composition has a bulk density between 0.2 g/cm3 and 0.8 g/cm3, such as between 0.3 g/cm3 and 0.8 g/cm3, such as between 0.4 g/cm3 and 0.8 g/cm3, such as between 0.5 and 0.8 g/cm3.

In an advantageous embodiment of the invention, the pouch composition comprises water and water-insoluble fiber in a weight ratio of no more than 3.0, such as no more than 2.5, such as no more than 2.0, such as no more than 1.5, such as no more than 1.0.

In an embodiment, the pouch composition comprises water and water-insoluble fiber in a weight ratio of 3.0 to 0.2, such as 2.0 to 0.2, such as 2.0 to 1.0 or such as 1.5 to 0.5.

Thus, the weight ratio above has in the numerator the content of water in percentage by weight of the pouch composition, and in the denominator the content water-insoluble fiber in percentage by weight of the pouch composition.

Generally, the present inventors found that a too low water content contributed to an incomplete wetting of the pouch composition. This typically resulted in dry formulation with lumps, i.e. an undesirable mouthfeel. Moreover, it could contribute to a delay nicotine release due to the time delay before the pouch composition is wetted by saliva. On the other hand, it was found that a too high water content could lead to a too heavy feeling composition, including undesirable flowability. Including a glidant, such a silicon dioxide, may remedy at least partly such undesirable flowability and thus allow a higher water content.

Having a water content within the scope of this invention may facilitate a fast release within the initial fast release period, such as within the first 120 seconds, since the pouch is already wetted or partly wetted with water from start of use.

On the other hand, the water content should not be too high. Having a too high water content could influence the liquid diffusion both into the pouch as well as out of the pouch. A fully wetted pouch may have a lower liquid diffusion both into and out of the pouch when used, whereas as partly wetted pouch may have higher liquid diffusion both into and out of the pouch. A pouch with a low liquid diffusion may thus have a lower release of nicotine, e.g. after 10 minutes.

In an advantageous embodiment of the invention, the pouch composition has a water content of no more than 60% by weight of said pouch composition, such as no more than 50% by weight of said pouch composition, such as no more than 40% by weight of said pouch composition, such as no more than 30% by weight of said pouch composition.

In an advantageous embodiment of the invention, the pouch composition is a powdered composition.

In an advantageous embodiment of the invention, the pouch composition as an average particle size between 1 and 1200 micrometer, such as between 10 and 500 micrometers.

In an embodiment of the invention, the pouch composition has an average particle size of below 1200 micrometer.

In an embodiment of the invention, the pouch composition has an average particle size above 1 micrometer, such as above 10 micrometers, such as above 50 micrometers.

In an embodiment of the invention, all ingredients where sieves through a 1400-micron sieve.

In an embodiment of the invention, all ingredients where sieves through an 800-micron sieve.

In an advantageous embodiment of the invention, at least 50% by weight of the pouch composition is provided in particles having a particle size above 10 micrometers, such as between 10 and 500 micrometers.

A release profile of nicotine may be obtained which both comprises a fast release period and a sustained release period.

In an embodiment, the fast release period may refer to the initial 120 seconds of the nicotine release profile, whereas the sustained release period may refer to the subsequent period of the release profile until end of experiment or end of use, such as a period from 2 minutes until 30 minutes after initiation of use.

In an advantageous embodiment of the invention, the pouch composition is adapted to release at least 15% by weight of the free-base nicotine within a period of 120 seconds in contact with oral saliva, such as at least 20% by weight of the free-base nicotine, such as at least 30% by weight of the free-base nicotine, such as at least 40% by weight of the free-base nicotine, when provided in a pouch and the release measured as described in example 3K.

In an advantageous embodiment of the invention, the pouch composition is designed to release at least 50% by weight of the free-base nicotine within a period of 120 seconds in contact with oral saliva, when provided in a pouch. Preferably, the release is measured as described in example 3K.

In an embodiment of the invention, the pouch composition is adapted to release at least 15% by weight of the free-base nicotine within a period of 120 seconds, such as at least 20% by weight of the free-base nicotine, such as at least 30% by weight of the free-base nicotine, when provided in a pouch and exposed to the in vitro release experiment described in example 3L.

In an advantageous embodiment of the invention, the pouch composition is adapted to release at least 30% by weight of the free-base nicotine within a period of 10 minutes in contact with oral saliva, such as at least 40% by weight of the free-base nicotine, such as at least 50% by weight of the free-base nicotine, such as at least 60% by weight of the free-base nicotine, when provided in a pouch and the release measured as described in example 3K.

In an embodiment of the invention, the pouch composition is adapted to release at least 30% by weight of the free-base nicotine within a period of 10 minutes, such as at least 40% by weight of the free-base nicotine, such as at least 50% by weight of the free-base nicotine, such as at least 60% by weight of the free-base nicotine, when provided in a pouch and exposed to the in vitro release experiment described in example 3L.

Release rate describes the average release of nicotine per minute within a given period.

In an embodiment of the invention, the pouch composition provided in a pouch to the oral cavity have a release rate of nicotine of at least 0.2% per minute within the release period from 2 to 10 minutes, such as at least 0.3% per minute within the release period from 2 to 10 minutes, such as at least 0.4% per minute within the release period from 2 to 10 minutes, such as at least 0.5% per minute within the release period from 2 to 10 minutes.

In an embodiment of the invention, the pouch composition provided in a pouch and exposed to the in vitro release experiment described in example 3L have a release rate of nicotine of at least 0.2% per minute within the release period of 2 to 60 minutes, such as at least 0.3% per minute within the release period of 2 to 60 minutes, such as at least 0.4% per minute within the release period of 2 to 60 minutes, such as at least 0.5% per minute within the release period of 2 to 60 minutes.

In an embodiment of the invention, the pouch composition provided in a pouch and exposed to the in vitro release experiment described in example 3L have a release rate of nicotine of at least 0.2% per minute within the release period of 2 to 30 minutes, such as at least 0.3% per minute within the release period of 2 to 30 minutes, such as at least 0.4% per minute within the release period of 2 to 30 minutes, such as at least 0.5% per minute within the release period of 2 to 30 minutes.

In an advantageous embodiment of the invention, the pouch composition provided in a pouch and exposed to the in vitro release experiment described in example 3L have a release rate of nicotine of at least 0.2% per minute within the release period of 2 to 10 minutes, such as at least 0.3% per minute within the release period of 2 to 10 minutes, such as at least 0.4% per minute within the release period of 2 to 10 minutes, such as at least 0.5% per minute within the release period of 2 to 10 minutes.

In an embodiment of the invention, the pouch composition provided in a pouch and exposed to the in vitro release experiment described in example 3L have a release rate of nicotine of at least 0.1 mg per minute within the release period of 2 to 60 minutes, such as at least 0.2 mg per minute within the release period of 2 to 60 minutes.

In an embodiment of the invention, the pouch composition provided in a pouch and exposed to the in vitro release experiment described in example 3L have a release rate of nicotine of at least 0.4 mg per minute within the release period of 2 to 10 minutes.

In an advantageous embodiment of the invention, the pouch composition further comprises nicotine as a nicotine salt and/or as a complex with an ion exchange resin, such as polacrilex resin.

In an advantageous embodiment of the invention, the pouch composition further comprises nicotine as a nicotine salt.

In an embodiment of the invention, the nicotine salt is selected from nicotine ascorbate, nicotine aspartate, nicotine benzoate, nicotine monotartrate, nicotine bitartrate, nicotine chloride (e.g., nicotine hydrochloride and nicotine dihydrochloride), nicotine citrate, nicotine fumarate, nicotine gensitate, nicotine lactate, nicotine mucate, nicotine laurate, nicotine levulinate, nicotine malate nicotine perchlorate, nicotine pyruvate, nicotine salicylate, nicotine sorbate, nicotine succinate, nicotine zinc chloride, nicotine sulfate, nicotine tosylate and hydrates thereof (e.g., nicotine zinc chloride monohydrate).

In an embodiment of the invention, the nicotine salt comprises or consists of nicotine bitartrate.

In an advantageous embodiment of the invention, the pouch composition further comprises nicotine as a complex with an ion exchange resin, such as polacrilex resin.

An advantage of the above embodiment may be that a desirable nicotine release profile may be obtained having both a nicotine release component with a relatively fast release due to the free-base nicotine, and a sustained release component due to the complex with nicotine and ion exchange resin.

In an embodiment of the invention, the pouch composition comprises free-base nicotine mixed with ion exchange resin combined with nicotine as a complex with an ion exchange resin, such as polacrilex resin.

In an embodiment of the invention, the pouch composition comprises free-base nicotine mixed with a water-soluble composition, such as sugar alcohol or water-soluble fiber, combined with nicotine as a complex with an ion exchange resin, such as polacrilex resin.

In an embodiment of the invention, the polacrilex resin is Amberlite®IRP64.

In an advantageous embodiment of the invention, the pouch composition further comprises a preservative.

The preservative may help to preserve the pouch composition against undesirable microbiological growths.

In an advantageous embodiment of the invention, the pouch composition further comprises a preservative in an amount of 0.05 to 0.5% by weight of the pouch composition, such as 0.1 to 0.2% by weight of the pouch composition.

Non-limiting examples of usable preservatives within the scope of the invention includes sorbic acid (E200) and salts thereof (e.g. sodium sorbate (E201), potassium sorbate (E202), calcium sorbate (E203)), benzoic acid (E210) and salts thereof (e.g. sodium benzoate (E211), potassium benzoate (E212), calcium benzoate (E213)).

In an advantageous embodiment of the invention, the pouch composition comprises less than 0.1% by weight of preservatives, such as less than 0.05% by weight of preservatives.

Thus, the pouch composition may comprise preservatives in an amount of 0 to 0.1% by weight of preservatives, such as in an amount of 0 to 0.05% by weight of preservatives. This includes zero content of preservatives, i.e. that the pouch composition is free of preservatives. The low amount or even absence of preservative may be realized by obtaining a relatively alkaline environment, particularly by the use of free-base nicotine.

In an advantageous embodiment of the invention, the pouch composition is free of preservatives.

The low amount or even absence of preservative may be realized by obtaining a relatively alkaline environment, particularly by the use of free-base nicotine.

In an embodiment of the invention, the pouch composition comprises antioxidant.

An advantage of the above embodiment may be that the nicotine may have a lower degree of degradation.

In an embodiment of the invention, the antioxidant is selected from butylated hydroxytoluene (BHT), butylated hydroxyanisole (BHA), Tocopherol, and combinations thereof. Other antioxidants may also be applied.

In an advantageous embodiment of the invention, the pouch composition comprises nicotine in an amount of at least 0.1% by weight of the pouch composition, such as at least 0.2% by weight of the pouch composition, such as at least 0.5% by weight of the pouch composition, such as at least 1.0% by weight of the pouch composition.

In an advantageous embodiment of the invention, the pouch composition comprises nicotine in an amount of no more than 20% by weight of the pouch composition, such as no more than 10% by weight of the pouch composition, such as no more than 5 by weight of the pouch composition.

In an embodiment of the invention, the pouch composition comprises nicotine in an amount of 0.1 to 20% by weight of the pouch composition, such as in an amount of 0.2 to 20% by weight of the pouch composition, such as in an amount of 0.5 to 10% by weight of the pouch composition.

In an advantageous embodiment of the invention, the pouch composition comprises nicotine in an amount corresponding to 0.5 to 20 mg per pouch, such as 1.0 to 20 mg per pouch, such as 5.0 to 15 mg per pouch.

In an advantageous embodiment of the invention, the pouch composition further comprises a release controlling composition.

In an advantageous embodiment of the invention, said release controlling composition is selected from the list consisting of metallic stearates, modified calcium carbonate, hydrogenated vegetable oils, partially hydrogenated vegetable oils, polyethylene glycols, polyoxyethylene monostearates, animal fats, silicates, silicates dioxide, talc, magnesium stearates, calcium stearates, fumed silica, powdered hydrogenated cottonseed oils, hydrogenated vegetable oils, hydrogenated soya oil, emulsifiers, triglycerides, and mixtures thereof.

In an embodiment of the invention, the pouch composition is free of triglycerides.

In an advantageous embodiment of the invention, the release controlling composition is hydrophobic.

In an advantageous embodiment of the invention, said release controlling composition comprises one or more metallic stearates, such as magnesium stearate and/or calcium stearate.

In an embodiment of the invention, said release controlling composition comprises magnesium stearate.

In an embodiment of the invention, said release controlling composition comprises calcium stearate.

In an advantageous embodiment of the invention, the pouch composition comprises said release controlling composition in an amount of between 1 and 20 percent by weight of said pouch composition.

In an embodiment of the invention the release controlling composition comprises or is a solubiliser, such as a solubiliser selected from the list of monoglycerides, diglycerides, polysorbate (e.g. Tween XX), sucrose-ester, and combinations thereof.

Anionic, cationic, amphoteric or non-ionic solubilisers can be used. Suitable solubilisers include lecithins, polyoxyethylene stearate, polyoxyethylene sorbitan fatty acid esters, fatty acid salts, mono and diacetyl tartaric acid esters of mono and diglycerides of edible fatty acids, citric acid esters of mono and diglycerides of edible fatty acids, saccharose esters of fatty acids, polyglycerol esters of fatty acids, polyglycerol esters of interesterified castor oil acid (E476), sodium stearoyllatylate, sodium lauryl sulfate and sorbitan esters of fatty acids and polyoxyethylated hydrogenated castor oil (e.g. the product sold under the trade name CREMOPHOR), block copolymers of ethylene oxide and propylene oxide (e.g. products sold under trade names PLURONIC and POLOXAMER), polyoxyethylene fatty alcohol ethers, polyoxyethylene sorbitan fatty acid esters, sorbitan esters of fatty acids and polyoxyethylene steraric acid esters.

Particularly suitable solubilisers are polyoxyethylene stearates, such as for instance polyoxyethylene(8)stearate and polyoxyethylene(40)stearate, the polyoxyethylene sorbitan fatty acid esters sold under the trade name TWEEN, for instance TWEEN 20 (monolaurate), TWEEN 80 (monooleate), TWEEN 40 (monopalmitate), TWEEN 60 (monostearate) or TWEEN 65 (tristearate), mono and diacetyl tartaric acid esters of mono and diglycerides of edible fatty acids, citric acid esters of mono and diglycerides of edible fatty acids, sodium stearoyllactylate, sodium laurylsulfate, polyoxyethylated hydrogenated castor oil, blockcopolymers of ethylene oxide and propyleneoxide and polyoxyethylene fatty alcohol ether. The solubiliser may either be a single compound or a combination of several compounds. The expression "solubiliser" is used in the present text to describe both possibilities; the solubiliser used must be suitable for use in food and/or medicine.

In an advantageous embodiment of the invention, the pouch composition is free of tobacco, tobacco fibers and fibers derived from tobacco.

In some alternative embodiments, the pouch composition may comprise minor amounts of tobacco. Any, nicotine provided as part of tobacco, such as e.g. powdered tobacco, is further to the free-base nicotine. Such tobacco may e.g. be included to provide tobacco flavor.

In an embodiment, the pouch composition may comprise tobacco, tobacco fibers, or fibers derived from tobacco in an amount of 0.1 to 5.0% by weight of the pouch composition, such as in an amount of 0.1 to 3.0% by weight of the pouch composition. Thus, while the pouch composition in some embodiments may comprise small amounts of tobacco, this is in addition to the free-base nicotine, and thus the pouch composition is not tobacco based.

In an embodiment of the invention, the pouch composition comprises less than 5.0% by weight of tobacco, such as less than 3.0% by weight of the pouch composition, such as less than 1.0% by weight of the pouch composition, such as less than 0.5% by weight of the pouch composition, such as less than 0.1% by weight of the pouch composition, such as being free of tobacco.

In an advantageous embodiment of the invention, the water-insoluble composition does not comprise tobacco, tobacco fibers or fibers derived from tobacco. Thus, in this embodiment, the water-insoluble fibers are non-tobacco fibers, i.e. does not comprise tobacco, tobacco fibers, or fibers derived from tobacco.

In an advantageous embodiment of the invention, the pouch composition is free of microcrystalline cellulose (MCC), such as free of cellulose.

In an embodiment of the invention, the pouch composition comprises cellulose and is free of microcrystalline cellulose (MCC).

In an advantageous embodiment of the invention, the pouch composition said composition comprises sugar alcohol selected from the group consisting of sorbitol, erythritol, xylitol, lactitol, maltitol, mannitol, hydrogenated starch hydrolyzates, isomalt, or any combination thereof and wherein the composition comprises said sugar alcohol in an amount of 1-80% by weight of the pouch composition, such as 5-70% by weight of the pouch composition, such as 10-60% by weight of the pouch composition.

In an advantageous embodiment of the invention, said pouch composition comprises sugar alcohol selected from the group consisting of sorbitol, erythritol, xylitol, lactitol, maltitol, mannitol, hydrogenated starch hydrolyzates, isomalt, or any combination thereof, wherein the composition comprises said sugar alcohol in an amount of 1-80% by weight of the pouch composition, such as 5-70% by weight of the pouch composition, such as 10-60% by weight of the pouch composition, and wherein said composition further comprises water-insoluble fibers in an amount of between 5 and 50% by weight of the pouch composition, such as between 10 and 30% by weight of the pouch composition.

In an advantageous embodiment of the invention, said pouch composition comprises sugar alcohol selected from the group consisting of sorbitol, erythritol, xylitol, lactitol, maltitol, mannitol, hydrogenated starch hydrolyzates, isomalt, or any combination thereof, wherein the composition comprises said sugar alcohol in an amount of 1-80% by weight of the pouch composition, such as 5-70% by weight of the pouch composition, such as 10-60% by weight of the pouch composition, wherein said composition further comprises water-insoluble fibers in an amount of between 5 and 50% by weight of the pouch composition, such as between 10 and 30% by weight of the pouch composition, and therein the water-insoluble composition comprises or consists of water-insoluble fiber, such as wheat fibers, oat fibers, pea fibers, powdered cellulose, or combinations thereof.

In an advantageous embodiment of the invention, said pouch composition comprises sugar alcohol selected from the group consisting of sorbitol, erythritol, xylitol, lactitol, maltitol, mannitol, hydrogenated starch hydrolyzates, isomalt, or any combination thereof, wherein the composition comprises said sugar alcohol in an amount of 1-80% by weight of the pouch composition, such as 5-70% by weight of the pouch composition, such as 10-60% by weight of the pouch composition, wherein said composition further comprises water-insoluble fibers in an amount of between 5 and 50% by weight of the pouch composition, such as between 10 and 30% by weight of the pouch composition, and wherein the water-insoluble composition comprises or consists of water-insoluble fiber, such as wheat fibers, oat fibers, pea fibers, powdered cellulose, or combinations thereof and wherein the pouch composition comprises flavor in an amount between 0.01 and 15% by weight of the pouch composition, such as between 0.1 and 15% by weight of the pouch composition, such as between 1 and 10% by weight of the pouch composition, such as between 3 and 10% by weight of the pouch composition.

In an advantageous embodiment of the invention, said pouch composition comprises sugar alcohol selected from the group consisting of sorbitol, erythritol, xylitol, lactitol, maltitol, mannitol, hydrogenated starch hydrolyzates, isomalt, or any combination thereof, wherein the composition comprises said sugar alcohol in an amount of 1-80% by weight of the pouch composition, such as 5-70% by weight of the pouch composition, such as 10-60% by weight of the pouch composition, wherein said composition further comprises water-insoluble fibers in an amount of between 5 and 50% by weight of the pouch composition, such as between 10 and 30% by weight of the pouch composition, wherein the water-insoluble composition comprises or consists of water-insoluble fiber, such as wheat fibers, oat fibers, pea fibers, powdered cellulose, or combinations thereof and wherein the pouch composition comprises flavor in an amount between 0.01 and 15% by weight of the pouch composition, such as between 0.1 and 15% by weight of the pouch composition, such as between 1 and 10% by weight of the pouch composition, such as between 3 and 10% by weight of the pouch composition and wherein the flavor is oil-based.

In an advantageous embodiment of the invention, said pouch composition comprises sugar alcohol selected from the group consisting of sorbitol, erythritol, xylitol, lactitol, maltitol, mannitol, hydrogenated starch hydrolyzates, isomalt, or any combination thereof, wherein the composition comprises said sugar alcohol in an amount of 1-80% by weight of the pouch composition, such as 5-70% by weight of the pouch composition, such as 10-60% by weight of the pouch composition, wherein said composition further comprises water-insoluble fibers in an amount of between 5 and 50% by weight of the pouch composition, such as between 10 and 30% by weight of the pouch composition, and wherein the pouch composition comprises a pH regulating agent selected from the group consisting of Acetic acid, Adipic acid, Citric acid, Fumaric acid, Glucono-δ-lactone, Gluconic acid, Lactic acid, Malic acid, Maleic acid, Tartaric acid, Succinic acid, Propionic acid, Ascorbic acid, Phosphoric acid, Sodium orthophosphate, Potassium orthophosphate, Calcium orthophosphate, Sodium diphosphate, Potassium diphosphate, Calcium diphosphate, Pentasodium triphosphate, Pentapotassium triphosphate, Sodium polyphosphate, Potassium polyphosphate, Carbonic acid, Sodium carbonate, Sodium bicarbonate, Potassium carbonate, Calcium carbonate, Magnesium carbonate, Magnesium oxide, or any combination thereof.

In an advantageous embodiment of the invention, said pouch composition comprises sugar alcohol selected from the group consisting of sorbitol, erythritol, xylitol, lactitol, maltitol, mannitol, hydrogenated starch hydrolyzates, isomalt, or any combination thereof, wherein the composition comprises said sugar alcohol in an amount of 1-80% by weight of the pouch composition, such as 5-70% by weight of the pouch composition, such as 10-60% by weight of the pouch composition, wherein said composition further comprises water-insoluble fibers in an amount of between 5 and 50% by weight of the pouch composition, such as between 10 and 30% by weight of the pouch composition, and wherein the pouch composition comprises a pH regulating agent which is a basic pH regulating agent, such as a basic buffering agent and/or such as Sodium carbonate, Sodium bicarbonate, Potassium carbonate, Potassium bicarbonate, Magnesium carbonate, or any combination thereof.

The invention further relates to an oral nicotine pouch product comprising a pouch and an amount of the nicotine pouch composition according to the invention or any of its embodiments enclosed in said pouch.

In an advantageous embodiment of the invention, said pouch product comprises said pouch composition in an amount of 50 to 1000 mg, such as 100 to 700 mg, such as 300 to 600 mg.

In an advantageous embodiment of the invention, said pouch product comprises nicotine in an amount of 0.5 to 20 mg, such as 1.0 to 20 mg, such as 5.0 to 15 mg.

In an advantageous embodiment of the invention, the pouch comprises a water-permeable membrane, comprising e.g. woven or non-woven fabric.

Typically, the pouch membrane comprise openings, where the characteristic opening dimension is adapted to a characteristic dimension of the pouch composition so as to retain the pouch composition inside the pouch before use and/or to retain a part of the pouch composition, such as an water-insoluble composition, inside the pouch during use.

In order to obtain a pouch membrane having suitable opening dimensions in view of the pouch composition to be used, the material for the pouch membrane may be selected accordingly, e.g. comprising e.g. woven and/or non-woven fabric.

In other words, according to the various embodiments, the pouch membrane allows passage of saliva and prevents or inhibits passage of undissolved composition and the water-insoluble fibers. The pouch membrane may be of any suitable material e.g. woven or non-woven fabric (e.g. cotton, fleece etc.), heat sealable non-woven cellulose, such as long fiber paper, or other polymeric materials such as a synthetic, semi-synthetic or natural polymeric material. An example of suitable material for the pouch membrane is paper made of pulp and a small amount of wet strength agent. A material suitable for use must provide a semi-permeable membrane layer to prevent the powder or composition from leaving the bag or pouch during use. Suitable materials are also those that do not have a significant impact on the release of nicotine from the pouch.

In more detail, regarding the material, the pouch membrane may be a natural, synthetic, semi-synthetic hydrophilic or hydrophobic membrane. It may be made from one or more biocompatible and physiologically acceptable polymeric material. Examples of suitable materials for the pouch membrane are cellulose acetate and derivatives thereof, carboxymethyl cellulose, polycellulose ester, other cellulose derivatives including ethylcellulose, propylcellulose, polyethylene, polypropylene, polystyrene, polyvinyl chloride, polyvinyl acetate, polymers of methacrylates and acrylates, natural rubber, polycarbonate, polyethylene terephthalate, polyester, polyamide and nylon. Other suitable materials are mentioned herein before.

Rayon fibers (i.e. regenerated cellulose), such as viscose rayon fibers may also be used, e.g. in combination with an acrylic polymer that acts as binder in the nonwoven material and provides for heat-sealing of the pouch membrane during manufacturing thereof. Other binders, such as one or more copolymers of vinyl acetate and acrylic acid ester, may also be used.

Suitable pouch membranes for are available under the trade names "taboka," CatchDry, Ettan, General, Granit, Goteborgs Rape, GrovSnus White, Metropol Kaktus, Mocca Anis, Mocca Mint, Mocca Wintergreen, Kicks, Probe, Prince, Skruf, TreAnkrare, Camel Snus Original, Camel Snus Frost and Camel Snus Spice. The pouch membrane provides a liquid-permeable container of a type that may be considered to be similar in character to the mesh-like type of material that is used for the construction of a tea bag. Desired components of the nicotine composition to be released diffuse through the pouch membrane and into the mouth of the user.

Materials of the pouch membrane may have the form of a mesh, screen, perforated paper, permeable fabric, or the like. For example, pouch material manufactured from a mesh-like form of rice paper, or perforated rice paper, may dissolve in the mouth of the user. In some exemplary embodiments, the materials of the pouch membrane may be manufactured using water dispersible film forming materials (e.g., binding agents such as alginates, carboxymethylcellulose, xanthan gum, pullulan, and the like), as well as those materials in combination with materials such as ground cellulosics (e.g., fine particle size wood pulp). Preferred pouch materials, though water dispersible or dissolvable, may be designed and manufactured such that under conditions of normal use, a significant amount of the nicotine contents permeates through the pouch material prior to the time that the pouch undergoes loss of its physical integrity. If desired, flavoring ingredients, disintegration aids, and other desired components, may be incorporated within, or applied to, the pouch material.

Examples of various types of pouch membrane materials set forth in U.S. Pat. No. 5,167,244 to Kjerstad. Fleece materials for use as pouch membranes are described e.g. in WO 2008/152469, GB 673,587, and EP 2 692 254.

In an embodiment of the invention the membrane comprises water insoluble fiber of different origin than the water insoluble fiber contained in the pouched product.

In an embodiment of the invention both the water insoluble fiber of the membrane and the water-insoluble fiber of the pouch composition comprises natural fiber.

In an embodiment of the invention both the water insoluble fibers of the membrane and the water-insoluble fibers of the pouch composition are natural fibers.

In an advantageous embodiment of the invention, the pouched product comprises said pouch in an amount of up to 20 percent by weight of said pouched product, such as in an amount of up to 15 percent by weight of said pouched product.

In an advantageous embodiment of the invention, the pouched product comprises said pouch in an amount of 3-20 percent by weight of said pouched product, such as in an amount of 5-15 percent by weight of said pouched product.

In an advantageous embodiment of the invention, the free-base nicotine comprises free-base nicotine mixed with ion exchange resin in a weight ratio between the free-base nicotine and the ion exchange resin of 0.1 to 2.0, wherein the water-insoluble composition comprises or consists of water-insoluble fiber, such as a water-insoluble plant fiber, such as wheat fibers, oat fibers, pea fibers, rice fiber, maize fibers, tomato fibers, barley fibers, rye fibers, sugar beet fibers, buckwheat fibers, potato fibers, cellulose fibers, apple fibers, cocoa fibers, cellulose fiber, bamboo fibers, powdered cellulose, bran fibers or combinations thereof, wherein the pouch composition comprises sugar alcohol in an amount of 1-80% by weight of the pouch composition, and the pouch composition comprises pH regulating agent in an amount between 0.01 and 15% by weight of the pouch composition.

The invention further relates to a method of manufacturing the oral nicotine pouch product according to the invention or any of its embodiments, the method comprising the steps of providing the nicotine pouch composition according to the invention or any of its embodiments, providing the pouch, adding the pouch composition to said pouch, and sealing the pouch.

DETAILED DESCRIPTION OF THE INVENTION

As used herein the term "nicotine pouch composition" refers to the composition for use in an oral nicotine pouch, i.e. in pouches for oral use comprising nicotine. Also, the terms "nicotine pouch composition" and "pouch composition" is used interchangeably.

As used herein the term "free-base nicotine" refers to non-protonated form of nicotine, and therefore does not include nicotine salts and nicotine provided as a complex between nicotine and an ion exchange resin. Nevertheless, the free-base nicotine may be mixed with an amount of ion exchange resin or water-soluble compositions such as sugar alcohols or water-soluble fibers. While free-base nicotine includes both free-base nicotine extracted from tobacco as well as synthetically manufactured free-base nicotine, the free-base nicotine is not provided in the form of tobacco or powdered tobacco. Typically, free-base nicotine is provided as a liquid.

As used herein the term "pouch" is intended to mean a container typically formed by a web of a fibrous material enclosing a cavity. The pouch is pouch designed for administration of an active ingredient in the oral cavity, and thus it is adapted for oral use, it is non-toxic and not water-soluble. The fibrous material may e.g. form a woven or non-woven web or fabric. The pouch may for example be sealed by bonding two corresponding pieces of web or fabric to each other along their edges to form a cavity for the nicotine and the non-water-soluble composition. In order to release the nicotine, the pouch is made water-permeable so as to allow saliva from the oral cavity to penetrate the pouch and enter the cavity, where the saliva can come into contact with the nicotine, whereby the nicotine are released from the oral pouch.

As used herein the term "powder composition" refers to composition in the form of powder, i.e. as a particulate material having a relatively small particle size, for example between 1 and 1200 micrometer. Particularly, by powder composition is not meant a powdered tobacco.

As used herein the term "humectant" is understood as a moistening agent used to attract moisture or water in the form of saliva. Humectants may typically include suitably hygroscopic compositions. In some cases, humectants may also be described as moistening agents, due to their role in attraction of moisture. Examples of humectants include glycerol, propylene glycol, alginate, triacetin modified starch, hydroxypropyl cellulose, pectin, xanthan gum, etc.

As used herein the term "water-soluble" refers to a relatively high water-solubility, for example a water-solubility of more than 5 gram of water-soluble composition or substance per 100 mL of water measured at 25 degrees Celsius and pH of 7.0. When referring to a "soluble" composition or substance, water-soluble is meant, unless otherwise stated.

As used herein the term "water-insoluble" refers to relatively low water-solubility, for example a water-solubility of less than 0.1 gram of water-soluble composition or substance per 100 mL of water measured at 25 degrees Celsius and pH of 7.0. When referring to "insoluble", water-insoluble is meant unless otherwise stated.

As used herein the term "flavor" is understood as having its ordinary meaning within the art. Flavor includes liquid and powdered flavors. Thus, flavors do of course not include sweeteners (such as sugar, sugar alcohols and high intensity sweeteners), or acids providing pure acidity/sourness, nor compounds providing pure saltiness (e.g. NaCl) or pure bitterness. Flavor enhancers include substances that only provide saltiness, bitterness or sourness. Flavor enhancers thus include e.g. NaCl, Citric acid, ammonium chloride etc.

The pouches of the invention provide a nicotine release into the oral cavity. A release profile of nicotine may be obtained which both comprises a fast release period and a sustained release period.

As used herein the term "fast release" or "fast release period" may refer to the initial 2 minutes of the nicotine release profile, whereas the term "sustained release period refers" to the subsequent period of the release profile until end of experiment or end of use.

As used herein "release rate" describes the average release of nicotine per minute within a given period, for example if a pouch in the period from 2 minutes to 10 minutes further releases 16% of the nicotine dose, the release rate is 2% per minute within this given period. Alternatively, if a pouch in the period from 2 minutes to 10 minutes further releases 2 mg of nicotine, the release rate is 0.25 mg per minute within this given period. The release rate is determined only from the release data at the outer time points of the time period.

Typically, the pouches comprise openings, where the characteristic opening dimension is adapted to a characteristic dimension of the matrix composition so as to retain the matrix composition inside the pouch before use and/or to retain a part of the matrix composition, such as an water-insoluble composition, inside the pouch during use.

In order to obtain a pouch having suitable opening dimensions in view of the matrix composition to be used, the material for the pouch may be selected accordingly, e.g. comprising e.g. woven and/or non-woven fabric.

In other words, according to the various embodiments, the pouch forms a membrane allowing passage of saliva and prevents or inhibits passage of said matrix composition. The membrane of the pouch may be of any suitable material e.g. woven or non-woven fabric (e.g. cotton, fleece etc.), heat sealable non-woven cellulose or other polymeric materials such as a synthetic, semi-synthetic or natural polymeric material. An example of suitable pouch material is paper made of pulp and a small amount of wet strength agent. A material suitable for use must provide a semi-permeable membrane layer to prevent the powder or composition from leaving the bag or pouch during use. Suitable materials are also those that do not have a significant impact on the release of nicotine from the pouch.

The pouch composition is filled into pouches and is maintained in the pouch by a sealing. An ideal pouch is chemically and physically stable, it is pharmaceutically acceptable, it is insoluble in water, it is easy to fill with powder and seal, and it provides a semi-permeable membrane layer which prevent the powder from leaving the bag, but permit saliva and therein dissolved or sufficiently small suspended components from the pouch composition in the pouch, such as nicotine, to pass through said pouch.

The pouch may be placed in the oral cavity by the user. Saliva then enters into the pouch, and the nicotine and other components, which are soluble in saliva, start to dissolve and are transported with the saliva out of the pouch into the oral cavity, where the nicotine may be absorbed.

According to an embodiment of the invention, the pouch composition may further comprise one or more enhancers.

In an embodiment of the invention, said enhancers are selected from the group consisting of bile salts, cetomacrogols, chelating agents, citrates, cyclodextrins, detergents, enamine derivatives, fatty acids, labrasol, lecithins, phospholipids, syntetic and natural surfactants, nonionic surfactants, cell envelope disordering compounds, solvents, steroidal detergents, chelators, solubilization agents, charge modifying agents, pH regulating agents, degradative enzyme inhibitors, mucolytic or mucus clearing agents, membrane penetration-enhancing agents, modulatory agents of epithelial junction physiology, vasodilator agents, selective transport-enhancing agents, or any combination thereof. pH regulating agents include buffers.

In an embodiment of the invention, said enhancers are selected from the group consisting of cetylpyridinium chloride (CPC), benzalkonium chloride, sodium lauryl sulfate, polysorbate 80, Polysorbate 20, cetyltrimethylammonium bromide, laureth 9, sodium salicylate, sodium EDTA, EDTA, aprotinin, sodium taurocholate, saponins, bile salt derivatives, fatty acids, sucrose esters, azone emulsion, dextran sulphate, linoleic acid, labrafil, transcutol, urea, azone, nonionic surfactants, sulfoxides, sauric acid/PG, POE 23 lauryl ether, methoxysalicylate, dextran sulfate, methanol, ethanol, sodium cholate, Sodium taurocholate, Lysophosphatidyl choline, Alkylglycosides, polysorbates, Sorbitan esters, Poloxamer block copolymers, PEG-35 castor oil, PEG-40 hydrogenated castor oil, Caprocaproyl macrogol-8 glycerides, PEG-8 caprylic/capric, glycerides, Dioctyl sulfosuccinate, Polyethylene lauryl ether, Ethoxydiglycol, Propylene glycol, mono-di-caprylate, Glycerol monocaprylate, Glyceryl fatty acids (C$_8$-C$_{18}$) ethoxylated Oleic acid, Linoleic acid, Glyceryl caprylate/caprate, Glyceryl monooleate, Glyceryl monolaurate, Capryliccapric triglycerides, Ethoxylated nonylphenols, PEG-(8-50) stearates, Olive oil PEG-6, esters, Triolein PEG-6 esters, Lecithin, d-alpha tocopherol polyethylene glycol 1,000 succinate, Citric acid, Sodium citrate, BRIJ, Sodium laurate, 5-methoxysalicylic acid, Bile salts, Acetyl salicylate, ZOT, Docosahexaenoic acid, Alkylglycosides, Sodium glycocholate (GC-Na), Sodium taurocholate (TC-Na), EDTA, Choline salicylate, Sodium caprate (Cap-Na), N-lauryl-beta-D-maltopyranoside (LM), Diethyl maleate, Labrasol, Sodium salicylate, Mentol, Alkali metal alkyl sulphate, Sodium lauryl sulphate, Glycerin, Bile acid, Lecithin, phosphatidylcholine, phosphatidylserine, sphingomyelin, phophatidylethanolamine, cephalin, lysolecithin, Hyaluronic acid: alkalimetal salts, sodium, alkaline earth and aluminum, Octylphenoxypolyethoxyethanol, Glycolic acid, Lactic acid, Chamomile extract, Cucumber extract, Borage oil, Evening primrose oil, Polyglycerin, Lysine, Polylysine, Triolein, Monoolein, Monooleates, Monolaurates, Polydocanol alkyl ethers, Chenodeoxycholate, Deoxycholate, Glycocholic acid, Taurocholic acid, Glycodeoxycholic acid, Taurodeoxycholic acid, Sodium glycocholate, Phosphatidylcholine, Phosphatidylserine, Sphingomyelin, Phosphatidylethanolamine, Cephalin, Lysolecithin, Alkali metal hyaluronates, Chitosan, Poly-L-arginine, Alkyl glucoside, Saccharide alkyl ester, Fusidic acid derivatives, Sodium taurdihydrofusidate (STDHF), L-α-phosphatidylcholine Didecanoyl (DDPC), Nitroglycerine, nitropruside, N005 [3-(2-hydroxy-I-(methyl-ethyl)-2-nitrosohydrazino)-I-propanamine], NOC12 [iV-ethyl-2-(I-ethyl-hydroxy-2-nitrosohydrazino)-ethanamine, SNAP [S-nitroso-N-acetyl-DL-penicillamine, NORI, NOR4, deacylmethyl sulfoxide, azone, salicylamide, glyceryl-I,3-diacetoacetate,I,2-isopropylideneglycerine-3-acetoacetate), Amino acids, Amino acid salts, monoaminocarboxlic acids, Glycine, alanine, phenylalanine, proline, hydroxyproline, hydroxyamino acids, serine, acidic amino acids, aspartic acid, Glutamic acid, Basic amino acids, Lysine, N-acetylamino acids, N-acetylalanine, N-acetylphenylalanine, TM-acetylserine, N-acetylglycine, N-acetyllysine, N-acetylglutamic acid, N-acetylproline, N-acetylhydroxyproline, lactic acid, malic acid and citric acid and alkali metal salts thereof, pyrrolidonecarboxylic acids, alkylpyrrolidonecarboxylic acid esters, N-alkylpyrrolidones, proline acyl esters, sodium lauryl phosphate, sodium lauryl sulphate, sodium oleyl phosphate, sodium myristyl sulphate, polyoxyethylene alkyl ethers, polyoxyethylene alkyl esters, and caproic acid, alkylsaccharide, fusidic acid, polyethylene glycol, cetyl alcohol, polyvinylpyrolidone, Polyvinyl alcohol, Lanolin alcohol, Sorbitan monooleate, Ethylene glycol tetraacetic acid, Bile acid conjugate with taurine, Cholanic acid and salts, Cyclodextran, Cyclodextrin, Cyclodextrin (beta), Hydroxypropyl-β-cyclodetran, Sulfobutylether-β-cyclodextran, Methyl-β-cyclodextrin, Chitosan glutamate, Chitosan acetate, Chitosan hydrochloride, Chitosan hydrolactate, 1-O-alkyl-2-hydroxy-sn-glycero-3-phosphocholine, 3-O-alkyl-2-acetoyl-sn-glycero-1-phosphocholine,1-O-alkyl-2-O-acetyl-sn-glycero-3-phospho(N,N,N-trimethyl)hexanolamine, Propylene glycol, Tetradecylmaltoside (TDM), Sucrose dedecanoate.

According to an embodiment of the invention, the enhancer comprises one or more pH-regulating agent, such as a buffering agent.

In an embodiment of the invention, said pH-regulating agents are selected from the group consisting of Acetic acid, Adipic acid, Citric acid, Fumaric acid, Glucono-δ-lactone, Gluconic acid, Lactic acid, Malic acid, Maleic acid, Tartaric acid, Succinic acid, Propionic acid, Ascorbic acid, Phosphoric acid, Sodium orthophosphate, Potassium orthophosphate, Calcium orthophosphate, Sodium diphosphate, Potassium diphosphate, Calcium diphosphate, Pentasodium triphosphate, Pentapotassium triphosphate, Sodium polyphosphate, Potassium polyphosphate, Carbonic acid, Sodium carbonate, Sodium bicarbonate, Potassium carbonate, Calcium carbonate, Magnesium carbonate, Magnesium oxide, or any combination thereof.

According to various embodiments of the invention, one or more sugar alcohols may be included in the pouch as part of the pouch composition, e.g. as a carrier or part thereof, as a humectant, or as a sweetener. Suitable sugar alcohols include sugar alcohols selected from the group of sorbitol, erythritol, xylitol, lactitol, maltitol, mannitol, hydrogenated starch hydrolyzates, isomalt, or any combination thereof.

In an embodiment of the invention the pouch composition comprises high intensity sweetener.

Preferred high intensity sweeteners include, but are not limited to sucralose, aspartame, salts of acesulfame, such as acesulfame potassium, alitame, saccharin and its salts, cyclamic acid and its salts, glycyrrhizin, dihydrochalcones, thaumatin, monellin, stevioside and the like, alone or in combination.

In an embodiment of the invention, the pouch composition comprises bulk sweeteners including sugar and/or sugarless components.

In an embodiment of the invention, the pouch composition comprises bulk sweetener in the amount of 1.0 to about 80% by weight of the pouch composition, more typically constitute 5 to about 70% by weight of the pouch composition, and more commonly 10 to 60% by weight of the pouch composition or 10-50% by weight of the pouch composition. Bulk sweeteners may function both as a sweetener and also as a humectant. In some embodiments, inclusion of certain ingredients may limit the about amounts of bulk sweetener further.

The sweeteners may often support the flavor profile of the pouch composition.

Sugar sweeteners generally include, but are not limited to saccharide-containing components commonly known in the art of pouches, such as sucrose, dextrose, maltose, saccharose, lactose, sorbose, dextrin, trehalose, D-tagatose, dried invert sugar, fructose, levulose, galactose, corn syrup solids, glucose syrup, hydrogenated glucose syrup, and the like, alone or in combination. These sugar sweeteners may also be included as a humectant.

The sweetener can be used in combination with sugarless sweeteners. Generally, sugarless sweeteners include components with sweetening characteristics but which are devoid of the commonly known sugars and comprise, but are not limited to, sugar alcohols, such as sorbitol, mannitol, xylitol, hydrogenated starch hydrolyzates, maltitol, isomalt, erythritol, lactitol and the like, alone or in combination. These sugarless sweeteners may also be included as a humectant.

In an embodiment of the invention the pouch composition comprises flavor. Flavor may typically be present in amounts between 0.01 and 15% by weight of the total composition of the pouch, such as between 0.01 and 5% by weight of the total composition.

Non-exhaustive examples of flavors suitable in embodiments of the present invention are coconut, coffee, chocolate, vanilla, grape fruit, orange, lime, menthol, liquorice, caramel aroma, honey aroma, peanut, walnut, cashew, hazelnut, almonds, pineapple, strawberry, raspberry, tropical fruits, cherries, cinnamon, peppermint, wintergreen, spearmint, eucalyptus, and mint, fruit essence such as from apple, pear, peach, strawberry, apricot, raspberry, cherry, pineapple, and plum essence. The essential oils include peppermint, spearmint, menthol, eucalyptus, clove oil, bay oil, anise, thyme, cedar leaf oil, nutmeg, and oils of the fruits mentioned above.

In various embodiments of the invention, the pouch composition comprises a release controlling composition for controlling the release of the pouch composition and/or parts thereof, especially the nicotine.

The release controlling composition may, according to various embodiments, be selected group consisting of metallic stearates, modified calcium carbonate, hydrogenated vegetable oils, partially hydrogenated vegetable oils, polyethylene glycols, polyoxyethylene monostearates, animal fats, silicates, silicates dioxide, talc, magnesium stearates, calcium stearates, fumed silica, powdered hydrogenated cottonseed oils, hydrogenated vegetable oils, hydrogenated soya oil, emulsifiers, triglycerides, and mixtures thereof. Particularly, metallic stearates, such as magnesium stearate, may be advantageous.

The release controlling composition may be added to the pouch composition in various ways.

For example, the release controlling composition may be added by full powder mixture during the last few minutes of the final mixing.

Alternatively, the release controlling composition may be added after granulation steps on a granulation premix.

Still further, the release controlling composition may be added only as a fraction of the pouch composition so two different release profiles of nicotine is achieved. Even further two or more fractions of the matrix composition may comprise different amounts of the release controlling composition, if any, thereby providing a more complex and tailored release profile of nicotine.

The release controlling composition, such as magnesium stearate, may have a sealing effect and can be used to control the release of the nicotine and the solubility of the pouch.

According to an embodiment of the invention, the pouch composition comprises polyvinylpyrrolidone (PVP). The pouch composition may also be free of PVP.

One advantage of the above embodiment may be that a more uniform composition may be obtained.

EXAMPLES

Example 1A—Preparation of Pouches Designed for Administration of Nicotine

The material of the pouches is heat sealable non-woven cellulose, such as long fiber paper. Pouches that are not in form of non-woven cellulose fabric may also be used according to the invention.

The powder is filled into pouches and is maintained in the pouch by a sealing.

Example 1B—Preparation of Pouches Designed for Administration of Nicotine

The material of the pouches is manufactured using rayon fibers, such as viscose rayon staple fibers. The pouch membrane is heat sealed along its edges except for an opening in one end into an inner cavity formed by the pouch membrane.

The powder is filled into pouches and is maintained in the pouch by a sealing.

Example 2A—Nicotine Premix I—Resin

A Stephan mixer (vacuum premixing) was charged with water, and nicotine was weighed and added, the mixer was closed and stirred for 5 minutes. Then ion exchange resin Amberlite® IRP64 was weighed and added to the mixer. The mixer was closed and stirred for 10-60 minutes.

Thereby, a mixture of nicotine and cation exchange resin was produced from the constituents stated in the below table 1.

TABLE 1

Ingredients used to manufacture nicotine premix I.

| Constituent | Amount (kg) | Amount (%) |
|---|---|---|
| Nicotine | 1.0 | 5.7 |
| Water | 12.5 | 71.4 |
| Resin | 4.0 | 22.9 |
| Total | 17.5 | 100.0 |

Nicotine:resin ratio: 1:4 (0.25)
% water in obtained nicotine-resin composition: 71.4

Example 2B—Nicotine Premix II—Resin

A 60 liter planetary Bear Varimixer mixer was charged with water, and nicotine was weighed and added. The mixer was stirred at low speed for 1 minute at ambient temperature. Then ion exchange resin Amberlite® IRP64 was weighed and added to the mixer. The mixer was closed, stirred at high speed for 5 minutes, opened and scraped down, if necessary. Finally the mixer was stirred for further 5 minutes at high speed.

Thereby, a mixture of nicotine and cation exchange resin was produced from the constituents stated in the below table 2.

TABLE 2

Ingredients used to manufacture nicotine premix II.

| Constituent | Amount (kg) | Amount (%) |
|---|---|---|
| Nicotine | 1.08 | 13.2 |
| Water | 2.80 | 34.1 |
| Resin | 4.32 | 52.7 |
| Total | 8.20 | 100.0 |

Nicotine:resin ratio: 1:4 (0.25)
% water in obtained nicotine-resin composition: 34.1
The total process time was 20 minutes.

Example 2C—Nicotine Premix III—Resin

A 60 liter planetary Bear Varimixer mixer was charged with water, and nicotine was weighed and added. The mixer was stirred at low speed for 1 minute at ambient temperature. Then ion exchange resin Amberlite® IRP64 was weighed and added to the mixer. The mixer was closed, stirred at high speed for 5 minutes, opened and scraped down, if necessary. Finally the mixer was stirred for further 5 minutes at high speed.

Thereby, a mixture of nicotine and cation exchange resin was produced from the constituents stated in the below table 3.

TABLE 3

Ingredients used to manufacture nicotine premix III.

| Constituent | Amount (kg) | Amount (%) |
|---|---|---|
| Nicotine | 1.08 | 18.5 |
| Water | 0.44 | 7.5 |
| Resin | 4.32 | 74.0 |
| Total | 5.84 | 100.0 |

Nicotine:resin ratio: 1:4 (0.25)
% water in obtained nicotine-resin composition: 7.5
The total process time was 20 minutes.

Example 2D—Nicotine Premix IV—Resin

A 60 liter planetary Bear Varimixer mixer was charged with water, and nicotine was weighed and added. The mixer was stirred at low speed for 1 minute at ambient temperature. Then ion exchange resin Amberlite® IRP64 was weighed and added to the mixer. The mixer was closed, stirred at high speed for 5 minutes, opened and scraped down, if necessary. Finally the mixer was stirred for further 5 minutes at high speed.

Thereby, a mixture of nicotine and cation exchange resin was produced from the constituents stated in the below table 4.

TABLE 4

| Ingredients used to manufacture nicotine premix IV. | | |
| --- | --- | --- |
| Constituent | Amount (kg) | Amount (%) |
| Nicotine | 1.08 | 10.0 |
| Water | 5.40 | 50.0 |
| Resin | 4.32 | 40.0 |
| Total | 10.8 | 100.0 |

Nicotine:resin ratio: 1:4 (0.25)
% water in obtained nicotine-resin composition: 50.0
The total process time was 20 minutes.

Example 2E—Nicotine Premix V—Resin

A 60 liter planetary Bear Varimixer mixer was charged with water, and nicotine was weighed and added. The mixer was stirred at low speed for 1 minute at ambient temperature. Then ion exchange resin Amberlite® IRP64 was weighed and added to the mixer. The mixer was closed, stirred at high speed for 5 minutes, opened and scraped down, if necessary. Finally, the mixer was stirred for further 5 minutes at high speed.

Thereby, a mixture of nicotine and cation exchange resin was produced from the constituents stated in the below table 4B.

TABLE 4B

| Ingredients used to manufacture nicotine premix V. | | |
| --- | --- | --- |
| Constituent | Amount (kg) | Amount (%) |
| Nicotine | 1.78 | 20.0 |
| Water | 2.80 | 31.5 |
| Resin | 4.32 | 48.5 |
| Total | 8.90 | 100.0 |

Nicotine:resin ratio: 1:2.43 (0.41)
% water in obtained nicotine-resin composition: 31.5
The total process time was 20 minutes.

Example 2F—Nicotine Premix VI—Resin

A 60 liter planetary Bear Varimixer mixer was charged with water, and nicotine was weighed and added. The mixer was stirred at low speed for 1 minute at ambient temperature. Then ion exchange resin Amberlite® IRP64 was weighed and added to the mixer. The mixer was closed, stirred at high speed for 5 minutes, opened and scraped down, if necessary. Finally, the mixer was stirred for further 5 minutes at high speed.

Thereby, a mixture of nicotine and cation exchange resin was produced from the constituents stated in the below table 4C.

TABLE 4C

| Ingredients used to manufacture nicotine premix V. | | |
| --- | --- | --- |
| Constituent | Amount (kg) | Amount (%) |
| Nicotine | 3.05 | 30.0 |
| Water | 2.80 | 27.5 |
| Resin | 4.32 | 42.5 |
| Total | 10.17 | 100.0 |

Nicotine:resin ratio: 1:1.4 (0.71)
% water in obtained nicotine-resin composition: 27.5
The total process time was 20 minutes.

Example 2G—Nicotine Premix VII—Resin

A 60 liter planetary Bear Varimixer mixer was charged with water, and nicotine was weighed and added. The mixer was stirred at low speed for 1 minute at ambient temperature. Then ion exchange resin Amberlite® IRP64 was weighed and added to the mixer. The mixer was closed, stirred at high speed for 5 minutes, opened and scraped down, if necessary. Finally, the mixer was stirred for further 5 minutes at high speed.

Thereby, a mixture of nicotine and cation exchange resin was produced from the constituents stated in the below table 4A.

TABLE 4D

| Ingredients used to manufacture nicotine premix V. | | |
| --- | --- | --- |
| Constituent | Amount (kg) | Amount (%) |
| Nicotine | 5.15 | 42.0 |
| Water | 2.80 | 22.8 |
| Resin | 4.32 | 35.2 |
| Total | 12.27 | 100.0 |

Nicotine:resin ratio: 1.19:1 (1.19)
% water in obtained nicotine-resin composition: 22.8
The total process time was 20 minutes.

Example 2H—Nicotine Premix VIII—Resin

A 60 liter planetary Bear Varimixer mixer was charged with water, and nicotine was weighed and added. The mixer was stirred at low speed for 1 minute at ambient temperature. Then ion exchange resin Amberlite® IRP64 was weighed and added to the mixer. The mixer was closed, stirred at high speed for 5 minutes, opened and scraped down, if necessary. Finally, the mixer was stirred for further 5 minutes at high speed.

Thereby, a mixture of nicotine and cation exchange resin was produced from the constituents stated in the below table 4A.

TABLE 4E

| Ingredients used to manufacture nicotine premix V. | | |
| --- | --- | --- |
| Constituent | Amount (kg) | Amount (%) |
| Nicotine | 5.15 | 39.8 |
| Water | 2.80 | 21.6 |

TABLE 4E-continued

Ingredients used to manufacture nicotine premix V.

| Constituent | Amount (kg) | Amount (%) |
|---|---|---|
| Resin | 4.32 | 33.4 |
| Pea fiber | 0.67 | 5.2 |
| Total | 12.94 | 100.0 |

Nicotine:resin ratio: 1.19:1 (1.19)
% water in obtained nicotine-resin composition: 21.6
The total process time was 20 minutes.

Example 3A—Pouches

Comparative pouches containing nicotine polacrilex resin (NPR) or nicotine bitartrate (NBT) are prepared comprising powdered compositions as outlined in table 5. The pouches are made as follows.

Fibers and water are mixed using a planetary Bear Varimixer mixer for 5 minutes. Then, the following ingredients were added subsequently under continuous mixing: first Nicotine bitartrate xH2O (NBT, nicotine content of 32.5%) or nicotine polacrilex resin (NPR, nicotine content of 15.9%) as applicable (mixed for 2 minutes), then the remaining ingredients except liquid flavor and glidant if any (mixed for 2 minutes), then liquid flavor if any (mixed for 1 minute), then glidant if any (mixed for 1 minute). The total mixing time is 9-11 minutes.

The final powder composition is filled into pouches (target fill weight 500 mg powder per pouch). The pouch material of example 1A, made from long fiber paper, is used. The powder is filled into pouches and is maintained in the pouch by a sealing.

The material of the pouches is heat sealable non-woven cellulose, such as long fiber paper. Pouches that are not in form of non-woven cellulose fabric may also be used according to the invention.

The pouch material of example 1B may also be used.

The powder is filled into pouches and is maintained in the pouch by a sealing.

Pouches PPC1-PPC5 containing nicotine premix are prepared comprising powdered compositions as outlined in table 5. The pouches are made as follows.

Fibers and water are mixed using a planetary Bear Varimixer mixer for 5 minutes. Then, the following ingredients were added subsequently under continuous mixing: Nicotine premix (mixed for 2 minutes), then the remaining ingredients except liquid flavor and glidant if any (mixed for 2 minutes), then liquid flavor if any (mixed for 1 minute), then glidant if any (mixed for 1 minute). The total mixing time is 9-11 minutes.

The final powder composition is filled into pouches (target fill weight 500 mg powder per pouch). The pouch material of example 1A, made from long fiber paper, is used. The powder is filled into pouches and is maintained in the pouch by a sealing.

The material of the pouches is heat sealable non-woven cellulose, such as long fiber paper. Pouches that are not in form of non-woven cellulose fabric may also be used according to the invention.

The pouch material of example 1B may also be used.

The powder is filled into pouches and is maintained in the pouch by a sealing.

TABLE 5

| PPC | Comp. NBT | Comp. NPR | PPC1 | PPC2 | PPC3 | PPC4 | PPC5 |
|---|---|---|---|---|---|---|---|
| Amount of nicotine | 9.6 mg | 9.6 mg | 9.6 mg | 9.6 mg | 9.6 mg | 9.6 mg | 9.6 mg |
| Water content [wt %] | 30 | 30 | 30 | 25 | 15 | 10 | 40 |
| Raw material | Content in weight percent | | | | | | |
| NPR | — | 12.1 | — | — | — | — | — |
| NBT | 5.9 | — | — | — | — | — | — |
| Nicotine premix II | — | — | 14.6 | 14.6 | 14.6 | 14.6 | 14.6 |
| Xylitol DC | 15.0 | 8.8 | 11.3 | 16.3 | 26.3 | 31.3 | 1.3 |
| Purified water | 30 | 30 | 25 | 20 | 10 | 5 | 35 |
| Wheat fiber | 30 | 30 | 30 | 30 | 30 | 30 | 30 |
| Sodium alginate | 2.0 | 2.0 | 2.0 | 2.0 | 2.0 | 2.0 | 2.0 |
| Sodium carbonate | 5.0 | 5.0 | 5.0 | 5.0 | 5.0 | 5.0 | 5.0 |
| Flavor | 8.9 | 8.9 | 8.9 | 8.9 | 8.9 | 8.9 | 8.9 |
| NaCl | 0.1 | 0.1 | 0.1 | 0.1 | 0.1 | 0.1 | 0.1 |
| High intensity sweetener | 1.0 | 1.0 | 1.0 | 1.0 | 1.0 | 1.0 | 1.0 |
| Potassium sorbate | 0.1 | 0.1 | 0.1 | 0.1 | 0.1 | 0.1 | 0.1 |
| Silicon dioxide | 2.0 | 2.0 | 2.0 | 2.0 | 2.0 | 2.0 | 2.0 |
| Total | 100 | 100 | 100 | 100 | 100 | 100 | 100 |

The nicotine premix II (example 2B) comprises 34.1 wt % water, thereby contributing to the total water content.
Pouch content: 500 mg total, i.e. nicotine conc 19.2 mg/g
The Xylitol DC applied is e.g. trade name "Xylitab 200".

Wheat fiber, trade name "Vitacel 600 WF plus". Other fibers may be used as well, such as water-insoluble plant fibers, such as oat fibers, pea fibers, rice fiber, maize fibers, oat fibers, tomato fibers, barley fibers, rye fibers, sugar beet fibers, buckwheat fibers, potato fibers, cellulose fibers, apple fibers, cocoa fibers, powdered cellulose, bran fiber, bamboo fiber, and cellulose fiber.

For example, a mixture of e.g. menthol and peppermint may be used. Of course, other flavors as described herein may be use as well, in combination with menthol and/or peppermint or replacing these.

Silicon dioxide is used as a glidant. Other possible glidants include e.g. magnesium stearate, starch and talc.

Sodium carbonate is used as an alkaline buffering agent. Other buffering agents as described herein may also be used in combination with sodium carbonate or an alternative.

Potassium sorbate is used as a preservative. Other preservatives as described herein may also be used in combination with or instead of potassium sorbate.

Acesulfame potassium may as an example be used as high intensity sweeteners. Other usable high intensity sweeteners described herein may be used in combination with or instead of acesulfame potassium.

Pouches PPC1-PPC3, PPC5 show that different pouches having a water content of at least 15% by weight of the pouch composition can be made using free-base nicotine. Pouch PPC4 has a lower water content outside the scope of the invention. Comparative pouches Comp. NBT and Comp. NPR have a similar water content as PPC1, but uses nicotine salt and nicotine in complex with an ion exchange resin.

Example 3B—Pouches

Pouches PPC11-PPC15 are made similarly to pouches PPC1-PPC5 of example 3A. Pouches PPC11-PPC15 containing nicotine premix are prepared comprising powdered compositions as outlined in table 5. The pouches are made as follows.

Fibers and powder ingredients (except glidants) are mixed using a planetary Bear Varimixer mixer for 2 minutes. Then, Nicotine premix is added and mixed for 2 minutes. Water is then added and mixed for 5 minutes followed by liquid flavor (if any—mixed for 1 minute) and glidant (if any—mixed for 1 minute). The total mixing time is 9-11 minutes.

TABLE 6

| PPC | PPC11 | PPC12 | PPC13 | PPC14 | PPC15 | Comp. 2 |
|---|---|---|---|---|---|---|
| Amount of nicotine | 9.6 mg | 9.6 mg | 9.6 mg | 9.6 mg | 9.6 mg | 9.6 mg |
| Water content [wt %] | 30 | 25 | 15 | 10 | 35 | 5 |
| Raw material | | | Content in weight percent | | | |
| Nicotine premix II | 14.6 | 14.6 | 14.6 | 14.6 | 14.6 | 14.6 |
| Isomalt DC | 11.3 | 22.3 | 44.3 | 55.3 | 0.3 | 60.3 |
| Purified water | 25 | 20 | 10 | 5 | 30 | 0 |
| Wheat fiber | 30 | 24 | 12 | 6 | 36 | 6 |
| Sodium alginate | 2.0 | 2.0 | 2.0 | 2.0 | 2.0 | 2.0 |
| Sodium carbonate | 5.0 | 5.0 | 5.0 | 5.0 | 5.0 | 5.0 |
| Flavor | 9.0 | 9.0 | 9.0 | 9.0 | 9.0 | 9.0 |
| High intensity sweetener | 1.0 | 1.0 | 1.0 | 1.0 | 1.0 | 1.0 |
| Potassium sorbate | 0.1 | 0.1 | 0.1 | 0.1 | 0.1 | 0.1 |
| Silicon dioxide | 2.0 | 2.0 | 2.0 | 2.0 | 2.0 | 2.0 |
| Total | 100 | 100 | 100 | 100 | 100 | 100 |

The nicotine premix II comprises 34.1 wt % water, thereby contributing to the total water content.
Pouch content: 500 mg total.
The applied Isomalt DC e.g. GalenIQ 720.

Wheat fiber, trade name "Vitacel 600 WF plus". Other fibers may be used as well, such as water-insoluble plant fibers, such as oat fibers, pea fibers, rice fiber, maize fibers, oat fibers, tomato fibers, barley fibers, rye fibers, sugar beet fibers, buckwheat fibers, potato fibers, cellulose fibers, apple fibers, cocoa fibers, powdered cellulose, bran fiber, bamboo fibers, and cellulose fiber.

For example, a mixture of e.g. menthol and peppermint may be used. Of course, other flavors as described herein may be use as well, in combination with menthol and/or peppermint or replacing these.

Silicon dioxide is used as a glidant. Other possible glidants include e.g. magnesium stearate, starch and talc.

Sodium carbonate is used as an alkaline buffering agent. Other buffering agents as described herein may also be used in combination with sodium carbonate or an alternative.

Potassium sorbate is used as a preservative. Other preservatives as described herein may also be used in combination with or instead of potassium sorbate.

Acesulfame potassium may as an example be used as high intensity sweeteners. Other usable high intensity sweeteners described herein may be used in combination with or instead of acesulfame potassium.

Pouches PPC11-PPC13, PPC15 shows varying water content of at least 15% by weight of the pouch composition. The water content varies, but the ratio between the amount of added purified water and the amount of fibers remain constant.

Pouches PPC14 has a water content outside the scope of the invention and is used for comparative purposes.

Example 3C—Pouches

Pouches PPC21-PPC25 are made similarly to pouches PPC11-PPC15 of example 3B.

TABLE 7

| PPC | PPC21 | PPC22 | PPC23 | PPC24 | PPC25 | PPC26 |
|---|---|---|---|---|---|---|
| Amount of nicotine | 9.6 mg | 9.6 mg | 9.6 mg | 9.6 mg | 9.6 mg | 9.6 mg |
| Water content [wt %] | 30 | 30 | 30 | 30 | 30 | 30 |
| Raw material | | | Content in weight percent | | | |
| Nicotine premix II | 14.6 | 7.3 | 14.6 | 14.6 | 14.6 | 14.6 |
| Liquid nicotine* | — | 1.0 | — | — | — | — |
| Xylitol DC | 11.3 | 15.1 | 16.3 | 13.3 | 11.4 | 9.4 |
| Purified water | 25 | 27.5 | 25 | 25 | 25 | 25 |
| MCC (Avicel 102) | 30 | — | — | — | — | — |
| Wheat fiber | — | 30 | 30 | 30 | 30 | 30 |
| Sodium alginate | 2.0 | 2.0 | 2.0 | 2.0 | 2.0 | 2.0 |
| Sodium carbonate | 5.0 | 5.0 | — | 3.0 | 5.0 | 7.0 |
| Flavor | 9.0 | 9.0 | 9.0 | 9.0 | 9.0 | 9.0 |
| High intensity sweetener | 1.0 | 1.0 | 1.0 | 1.0 | 1.0 | 1.0 |
| Potassium sorbate | 0.1 | 0.1 | 0.1 | 0.1 | — | — |
| Silicon dioxide | 2.0 | 2.0 | 2.0 | 2.0 | 2.0 | 2.0 |
| Total | 100 | 100 | 100 | 100 | 100 | 100 |

*Liquid nicotine is added as a nicotine-sugar alcohol premix in powder form. The nicotine premix II comprises 34.1 wt % water, thereby contributing to the total water content.
Pouch content: 500 mg total.

Wheat fiber, trade name "Vitacel 600 WF plus". Other fibers may be used as well, such as water-insoluble plant fibers, such as oat fibers, pea fibers, rice fiber, maize fibers, oat fibers, tomato fibers, barley fibers, rye fibers, sugar beet fibers, buckwheat fibers, potato fibers, cellulose fibers, apple fibers, cocoa fibers, powdered cellulose, bran fiber, bamboo fibers, and cellulose fiber.

For example, a mixture of e.g. menthol and peppermint may be used. Of course, other flavors as described herein may be use as well, in combination with menthol and/or peppermint or replacing these.

Silicon dioxide is used as a glidant. Other possible glidants include e.g. magnesium stearate, starch and talc.

Sodium carbonate is used as an alkaline buffering agent. Other buffering agents as described herein may also be used in combination with sodium carbonate or an alternative.

Potassium sorbate is used as a preservative. Other preservatives as described herein may also be used in combination with or instead of potassium sorbate.

Acesulfame potassium may as an example be used as high intensity sweeteners. Other usable high intensity sweeteners described herein may be used in combination with or instead of acesulfame potassium.

Pouch PPC21 shows the use of e.g. microcrystalline cellulose (MCC) instead of wheat fibers.

Pouch PPC22 shows the use of a combination of nicotine-ion exchange resin premix and nicotine-sugar alcohol premix.

Pouches PPC23-PPC26 shows the use of different amounts of buffering agent (here sodium carbonate). For high amounts of basic buffering agents, achieving a more alkaline environment, there is less need for a preservative (here potassium sorbate), therefore it is omitted in PPC25-PPC26, having the highest amounts of alkaline buffering agents.

Example 3D—Pouches

Pouches PPC31-PPC32 are made similarly to pouches PPC1-PPC5 of example 3A, but using nicotine premix I and III, respectively.

Pouches PPC31-PPC35 are made as described below.

The nicotine and sugar alcohol (xylitol, sorbitol, maltitol or other) are weighed. The nicotine is slowly added to the sugar alcohol powder under stirring (Kitchenaid mixer operated at about 30 RPM in about 30 minutes). The resulting granulate is sieved and placed on a tray. The resulting powder is dried at ambient temperature overnight and is thereafter sieved to obtain a nicotine-sugar alcohol premix. It is also possible to add an amount of water to the nicotine before mixing with the sugar alcohol. Any such water will then be evaporated during the drying.

Fibers and water are mixed using a planetary Bear Varimixer mixer for 5 minutes. Then, the following ingredients were added subsequently under continuous mixing: Powder ingredients other than nicotine premix (mixed for 2 minutes), nicotine-sugar alcohol premix (mixed for 2 minutes), then liquid flavor if any (mixed for 1 minute) and finally glidant if any (mixed for 1 minute). The total mixing time is 9-11 minutes.

The final powder composition is filled into pouches (target fill weight 500 mg powder per pouch). The pouch material of example 1A, made from long fiber paper, is used. The powder is filled into pouches and is maintained in the pouch by a sealing.

The material of the pouches is heat sealable non-woven cellulose, such as long fiber paper. Pouches that are not in form of non-woven cellulose fabric may also be used according to the invention.

The pouch material of example 1B may also be used.

The powder is filled into pouches and is maintained in the pouch by a sealing.

TABLE 8

| | PPC | | | | | | |
|---|---|---|---|---|---|---|---|
| | PPC 31 | PPC 32 | PPC 33 | PPC 34 | PPC 35 | PPC 36 | PPC 37 |
| Amount of nicotine | 9.6 mg | 9.6 mg | 9.6 mg | 9.6 mg | 9.6 mg | 9.6 mg | 9.6 mg |
| Water content [wt %] | 30 | 30 | 30 | 30 | 30 | 30 | 30 |
| Raw material | Content in weight percent | | | | | | |
| Nicotine premix I | 33.7 | — | — | — | — | — | — |
| Nicotine premix III | — | 10.4 | — | — | — | — | — |
| Liquid nicotine* | — | — | 1.9 | 1.9 | 1.9 | 1.9 | 1.9 |
| Isomalt DC | 11.2 | 11.3 | 19.0 | — | — | — | — |
| Sorbitol DC | — | — | — | 19.0 | — | — | — |
| Maltitol DC | — | — | — | — | 19.0 | — | — |
| Inulin | — | — | — | — | — | 19.0 | — |
| Polydextrose | — | — | — | — | — | — | 19.0 |
| Purified water | 6 | 29.2 | 30 | 30 | 30 | 30 | 30 |

TABLE 8-continued

| | PPC | | | | | | |
|---|---|---|---|---|---|---|---|
| | PPC 31 | PPC 32 | PPC 33 | PPC 34 | PPC 35 | PPC 36 | PPC 37 |
| Wheat fiber | 30 | 30 | 30 | 30 | 30 | 30 | 30 |
| Sodium alginate | 2.0 | 2.0 | 2.0 | 2.0 | 2.0 | 2.0 | 2.0 |
| Sodium carbonate | 5.0 | 5.0 | 5.0 | 5.0 | 5.0 | 5.0 | 5.0 |
| Flavor | 9.0 | 9.0 | 9.0 | 9.0 | 9.0 | 9.0 | 9.0 |
| High intensity sweetener | 1.0 | 1.0 | 1.0 | 1.0 | 1.0 | 1.0 | 1.0 |
| Potassium sorbate | 0.1 | 0.1 | 0.1 | 0.1 | 0.1 | 0.1 | 0.1 |
| Silicon dioxide | 2.0 | 2.0 | 2.0 | 2.0 | 2.0 | 2.0 | 2.0 |
| Total | 100 | 100 | 100 | 100 | 100 | 100 | 100 |

* Liquid nicotine is added as a nicotine-sugar alcohol premix or as a nicotine-water-soluble fiber premix in powder form. The nicotine premix I comprises 71.4 wt % water, thereby contributing to the total water content. The nicotine premix II comprises 34.1 wt % water, thereby contributing to the total water content. The nicotine premix III comprises 7.5 wt % water, thereby contributing to the total water content.
Pouch content: 500 mg total.

Wheat fiber, trade name "Vitacel 600 WF plus". Other fibers may be used as well, such as water-insoluble plant fibers, such as oat fibers, pea fibers, rice fiber, maize fibers, oat fibers, tomato fibers, barley fibers, rye fibers, sugar beet fibers, buckwheat fibers, potato fibers, cellulose fibers, apple fibers, cocoa fibers, powdered cellulose, bran fibers, bamboo fibers, and cellulose fiber.

For example, a mixture of e.g. menthol and peppermint may be used. Of course, other flavors as described herein may be use as well, in combination with menthol and/or peppermint or replacing these.

Silicon dioxide is used as a glidant. Other possible glidants include e.g. magnesium stearate, starch and talc.

Sodium carbonate is used as an alkaline buffering agent. Other buffering agents as described herein may also be used in combination with sodium carbonate or an alternative.

Potassium sorbate is used as a preservative. Other preservatives as described herein may also be used in combination with or instead of potassium sorbate.

Acesulfame potassium may as an example be used as high intensity sweeteners. Other usable high intensity sweeteners described herein may be used in combination with or instead of acesulfame potassium.

Pouches PPC31-PPC32 show use of other nicotine premixes.

Pouches PPC33-PPC35 show use of nicotine pre-mixed with different sugar alcohol.

Pouches PPC36-PPC37 show use of nicotine pre-mixed with different water-soluble fibers.

Example 3E—Pouches

Pouches PPC41-PPC45 are made similarly to pouches PPC1-PPC5 of example 3A.

TABLE 9

| | PPC | | | | | |
|---|---|---|---|---|---|---|
| | PPC 41 | PPC 42 | PPC 43 | PPC 44 | PPC 45 | PPC 46 |
| Amount of nicotine | 4.8 mg | 7.2 mg | 9.6 mg | 12 mg | 9.6 mg | 9.6 mg |
| Water content [wt %] | 27.5 | 28.3 | 30 | 31.2 | 30 | 30 |

TABLE 9-continued

| Raw material | PPC 41 | PPC 42 | PPC 43 | PPC 44 | PPC 45 | PPC 46 |
|---|---|---|---|---|---|---|
| | Content in weight percent | | | | | |
| Nicotine premix II | 7.3 | 9.7 | 14.6 | 18.3 | 14.6 | 14.6 |
| Xylitol DC | 18.6 | 16.2 | 11.3 | 7.6 | 13.3 | 5 |
| Erythritol | — | — | — | — | — | 6.3 |
| Purified water | 25 | 25 | 25 | 25 | 25 | 25 |
| Wheat fiber | 30 | 30 | 30 | 30 | 30 | 30 |
| Sodium alginate | 2.0 | 2.0 | 2.0 | 2.0 | — | 2.0 |
| Sodium carbonate | 5.0 | 5.0 | 5.0 | 5.0 | 5.0 | 5.0 |
| Flavor | 9.0 | 9.0 | 9.0 | 9.0 | 9.0 | 8.9 |
| NaCl | — | — | — | — | — | 0.1 |
| High intensity sweetener | 1.0 | 1.0 | 1.0 | 1.0 | 1.0 | 1.0 |
| Potassium sorbate | 0.1 | 0.1 | 0.1 | 0.1 | 0.1 | 0.1 |
| Silicon dioxide | 2.0 | 2.0 | 2.0 | 2.0 | 2.0 | 2.0 |
| Total | 100 | 100 | 100 | 100 | 100 | 100 |

The nicotine premix II comprises 34.1 wt % water, thereby contributing to the total water content.
Pouch content: 500 mg total.

Wheat fiber, trade name "Vitacel 600 WF plus". Other fibers may be used as well, such as water-insoluble plant fibers, such as oat fibers, pea fibers, rice fiber, maize fibers, oat fibers, tomato fibers, barley fibers, rye fibers, sugar beet fibers, buckwheat fibers, potato fibers, cellulose fibers, apple fibers, cocoa fibers, powdered cellulose, bran fibers, bamboo fibers, and cellulose fiber.

For example, a mixture of e.g. menthol and peppermint may be used. Of course, other flavors as described herein may be use as well, in combination with menthol and/or peppermint or replacing these.

Silicon dioxide is used as a glidant. Other possible glidants include e.g. magnesium stearate, starch and talc.

Sodium carbonate is used as an alkaline buffering agent. Other buffering agents as described herein may also be used in combination with sodium carbonate or an alternative.

Potassium sorbate is used as a preservative. Other preservatives as described herein may also be used in combination with or instead of potassium sorbate.

Acesulfame potassium may as an example be used as high intensity sweeteners. Other usable high intensity sweeteners described herein may be used in combination with or instead of acesulfame potassium.

Pouches PPC41-PPC44 show use of different doses of nicotine, from 4.8 mg to 12 mg.

Pouch PPC45 shows pouch without alginate, otherwise comparable to pouch PPC43.

Example 3F—Pouches

Pouches PPC51-PPC53 are made as follows.

Fibers and powder ingredients (except nicotine containing powders and glidants) are mixed for 1 minute using a planetary Bear Varimixer mixer. Then, NPR and NBT is added and mixed for 2 minutes (if applicable). Nicotine premix is then added and mixed for 2 minutes. Subsequently, water is added and mixed for 5 minutes followed by liquid flavor (if any—mixed for 1 minute) and glidant (if any—mixed for 1 minute). The total mixing time is 9-11 minutes.

TABLE 10

| PPC | PPC51 | PPC52 | PPC53 |
|---|---|---|---|
| Amount of nicotine | 9.6 mg | 9.6 mg | 9.6 mg |
| Water content [wt %] | 30 | 30 | 30 |
| Raw material | Content in weight percent | | |
| NPR | — | 6.0 | 3.0 |
| NBT | 2.9 | — | 1.5 |
| Nicotine premix II | 7.3 | 7.3 | 7.3 |
| Isomalt DC | 15.2 | 12.1 | 13.6 |
| Purified water | 27.5 | 27.5 | 27.5 |
| Wheat fiber | 30 | 30 | 30 |
| Sodium carbonate | 5.0 | 5.0 | 5.0 |
| Flavor | 9.0 | 9.0 | 9.0 |
| High intensity sweetener | 1.0 | 1.0 | 1.0 |
| Potassium sorbate | 0.1 | 0.1 | 0.1 |
| Silicon dioxide | 2.0 | 2.0 | 2.0 |
| Total | 100 | 100 | 100 |

The nicotine premix II comprises 34.1 wt % water, thereby contributing to the total water content.
Pouch content: 500 mg total Wheat fiber, trade name "Vitacel 600 WF plus". Other fibers may be used as well, such as water-insoluble plant fibers, such as oat fibers, pea fibers, rice fiber, maize fibers, oat fibers, tomato fibers, barley fibers, rye fibers, sugar beet fibers, buckwheat fibers, potato fibers, cellulose fibers, apple fibers, cocoa fibers, powdered cellulose, bran fibers, bamboo fibers, and cellulose fiber.

For example, a mixture of e.g. menthol and peppermint may be used. Of course, other flavors as described herein may be use as well, in combination with menthol and/or peppermint or replacing these.

Silicon dioxide is used as a glidant. Other possible glidants include e.g. magnesium stearate, starch and talc.

Sodium carbonate is used as an alkaline buffering agent. Other buffering agents as described herein may also be used in combination with sodium carbonate or an alternative.

Potassium sorbate is used as a preservative. Other preservatives as described herein may also be used in combination with or instead of potassium sorbate.

Acesulfame potassium may as an example be used as high intensity sweeteners. Other usable high intensity sweeteners described herein may be used in combination with or instead of acesulfame potassium.

Pouch PPC51 shows pouch using nicotine-ion exchange resin premix in combination with nicotine bitartrate (NBT).

Pouch PPC52 shows pouch using nicotine-ion exchange resin premix in combination with nicotine polacrilex resin (NPR).

Pouch PPC53 shows pouch using nicotine-ion exchange resin premix in combination with nicotine bitartrate (NBT) and nicotine polacrilex resin (NPR).

Example 3G—Pouches

Pouches PPC61-PPC65 containing nicotine premix are prepared comprising powdered compositions as outlined in table 11. The pouches are made as follows.

Fibers and powder ingredients (except glidants) are mixed using a Lödige mixer for 2 minutes. Then, Nicotine premix is added and mixed for 2 minutes. With the mixer running, water is then added during a period of 15 minutes followed by liquid flavor (if any—mixed for 15 minutes) and glidant (if any—mixed for 1 minute). The total mixing time is 19-35 minutes.

TABLE 11

| | PPC 61 | PPC 62 | PPC 63 | PPC 64 | PPC 65 | PPC 66 | PPC 67 |
|---|---|---|---|---|---|---|---|
| Amount of nicotine | 9.6 mg | 9.6 mg | 9.6 mg | 9.6 mg | 9.6 mg | 9.6 mg | 9.6 mg |
| Water content [wt %] | 30 | 30 | 30 | 30 | 30 | 30 | 30 |
| Raw material | Content in weight percent | | | | | | |
| Nicotine premix VI | 6.4 | 6.4 | 6.4 | 6.4 | 6.4 | 6.4 | 6.4 |
| Xylitol | 5 | 18.3 | 18.3 | 18.3 | 5 | 5 | 5 |
| Erythritol | 13.5 | — | — | — | 13.5 | 13.5 | 13.5 |
| Purified water | 28 | 28 | 28 | 28 | 28 | 28 | 28 |
| Wheat fiber | 30 | 30 | 20 | 40 | 30 | 30 | 30 |
| Sodium alginate | 2.0 | 2.0 | 2.0 | 2.0 | 2.0 | — | — |
| Glycerol | — | — | — | — | — | 2.0 | — |
| Hydroxypropyl cellulose | — | — | — | — | — | — | 2.0 |
| Sodium carbonate | 5.0 | 3.0 | 3.0 | 3.0 | 3.0 | 3.0 | 3.0 |
| Sodium bicarbonate | — | 2.0 | 2.0 | 2.0 | 2.0 | 2.0 | 2.0 |
| Flavor | 7.0 | 7.0 | 7.0 | 7.0 | 7.0 | 7.0 | 7.0 |
| High intensity sweetener | 1.0 | 1.0 | 1.0 | 1.0 | 1.0 | 1.0 | 1.0 |
| Potassium sorbate | 0.1 | 0.1 | 0.1 | 0.1 | 0.1 | 0.1 | 0.1 |
| Silicon dioxide | 2.0 | 2.0 | 2.0 | 2.0 | 2.0 | 2.0 | 2.0 |
| Total | 100 | 100 | 100 | 100 | 100 | 100 | 100 |

The nicotine premix VI comprises 27.5 wt % water, thereby contributing to the total water content.
Pouch content: 500 mg total.

Wheat fiber, trade name "Vitacel 600 WF plus". Other fibers may be used as well, such as water-insoluble plant fibers, such as oat fibers, pea fibers, rice fiber, maize fibers, oat fibers, tomato fibers, barley fibers, rye fibers, sugar beet fibers, buckwheat fibers, potato fibers, cellulose fibers, apple fibers, cocoa fibers, powdered cellulose, bamboo fibers, bran fibers, and cellulose fiber.

For example, a mixture of e.g. menthol and peppermint may be used. Of course, other flavors as described herein may be use as well, in combination with menthol and/or peppermint or replacing these.

Silicon dioxide is used as a glidant. Other possible glidants include e.g. magnesium stearate, starch and talc.

Sodium alginate, glycerol and hydroxypropyl cellulose (HPC) may be used as humectants. Other humectants as described herein may also be used in combination with sodium alginate, glycerol or HPC or as an alternative.

Sodium carbonate and sodium bicarbonate are used as alkaline buffering agent. Other buffering agents as described herein may also be used in combination with sodium carbonate or an alternative.

Potassium sorbate is used as a preservative. Other preservatives as described herein may also be used in combination with or instead of potassium sorbate.

Acesulfame potassium and/or sucralose may as an example be used as high intensity sweeteners. Other usable high intensity sweeteners described herein may be used in combination with or instead of acesulfame potassium and/or sucralose.

Pouches PPC61-PPC62 show use of different sweetener and buffer combinations.

Pouches PPC63-PPC64 show pouches with varying fiber content.

Pouches PPC65-PPC67 show use of different humectants.

Example 3H—Pouches

Pouches PPC71-PPC76 containing nicotine premix are prepared comprising powdered compositions as outlined in table 12. The pouches are made as follows.

Fibers and powder ingredients (except glidants) are mixed using a Lödige mixer for 2 minutes. Then, Nicotine premix is added and mixed for 2 minutes. With the mixer running, water is then added during a period of 15 minutes followed by liquid flavor (if any—mixed for 15 minutes) and glidant (if any—mixed for 1 minute). The total mixing time is 19-35 minutes.

The final powder composition is filled into pouches (target fill weight 500 mg powder per pouch). The pouch material of example 1A, made from long fiber paper, is used. The powder is filled into pouches and is maintained in the pouch by a sealing. The pouch material of example 1B may also be used.

TABLE 12

| | PPC 71 | PPC 72 | PPC 73 | PPC 74 | PPC 75 | PPC 76 | PPC 77 |
|---|---|---|---|---|---|---|---|
| Amount of nicotine | 9.6 mg | 9.6 mg | 9.6 mg | 9.6 mg | 9.6 mg | 9.6 mg | 9.6 mg |
| Water content [wt %] | 30 | 30 | 30 | 30 | 30 | 30 | 30 |
| Raw material | Content in weight percent | | | | | | |
| Nicotine premix IV | 19.2 | — | — | — | — | — | — |
| Nicotine premix V | — | 9.6 | — | — | — | — | — |
| Nicotine premix VI | — | — | — | — | 6.4 | 6.4 | 6.4 |
| Nicotine premix VII | — | — | 4.6 | — | — | — | — |
| Nicotine premix VIII | — | — | — | 4.8 | — | — | — |
| Purified water | 21 | 27 | 29 | 29 | 28 | 28 | 28 |
| Wheat fiber | 30 | 30 | 30 | 29.75 | — | — | — |
| Oat fiber | — | — | — | — | 30 | — | — |
| Pea fiber | — | — | — | 0.25 | — | 30 | — |
| Powdered cellulose | — | — | — | — | — | — | 30 |
| Xylitol DC | 5.0 | 5.0 | 5.0 | 5.0 | 5.0 | 5.0 | 5.0 |
| Erythritol | 7.7 | 11.3 | 14.3 | 14.1 | 13.5 | 13.5 | 13.5 |
| Sodium alginate | 2.0 | 2.0 | 2.0 | 2.0 | 2.0 | 2.0 | 2.0 |
| Sodium carbonate | 5.0 | 5.0 | 5.0 | 5.0 | 5.0 | 5.0 | 5.0 |
| Flavor | 7.0 | 7.0 | 7.0 | 7.0 | 7.0 | 7.0 | 7.0 |
| High intensity sweetener | 1.0 | 1.0 | 1.0 | 1.0 | 1.0 | 1.0 | 1.0 |
| Potassium sorbate | 0.1 | 0.1 | 0.1 | 0.1 | 0.1 | 0.1 | 0.1 |
| Silicon dioxide | 2.0 | 2.0 | 2.0 | 2.0 | 2.0 | 2.0 | 2.0 |
| Total | 100 | 100 | 100 | 100 | 100 | 100 | 100 |

The nicotine premixes comprise water in varying amount, thereby contributing to the total water content.
Nicotine premix VIII comprises peafiber.
Pouch content: 500 mg total, i.e. nicotine conc 19.2 mg/g
Wheat fiber, trade name "Vitacel 600 WF plus".
Powdered cellulose, trade name "Vitacel L00" or "Vitacel L700G".
Oat fiber, trade name "Vitacel HF 600".
Pea fiber, trade name "Vitacel EF150".

Other fibers may be used as well, such as water-insoluble plant fibers, such as oat fibers, pea fibers, rice fiber, maize fibers, oat fibers, tomato fibers, barley fibers, rye fibers, sugar beet fibers, buckwheat fibers, potato fibers, cellulose fibers, apple fibers, cocoa fibers, powdered cellulose, bamboo fibers, bran fibers, and cellulose fiber.

For example, a mixture of e.g. menthol and peppermint may be used. Of course, other flavors as described herein may be use as well, in combination with menthol and/or peppermint or replacing these.

Silicon dioxide is used as a glidant. Other possible glidants include e.g. magnesium stearate, starch and talc.

Sodium alginate, glycerol and hydroxypropyl cellulose (HPC) may be used as humectants. Other humectants as described herein may also be used in combination with sodium alginate, glycerol or HPC or as an alternative.

Sodium carbonate and sodium bicarbonate are used as alkaline buffering agent. Other buffering agents as described herein may also be used in combination with sodium carbonate or an alternative.

Potassium sorbate is used as a preservative. Other preservatives as described herein may also be used in combination with or instead of potassium sorbate.

Acesulfame potassium and/or sucralose may as an example be used as high intensity sweeteners. Other usable high intensity sweeteners described herein may be used in combination with or instead of acesulfame potassium and/or sucralose.

Pouches PPC71-PPC74 show use of different nicotine premixes.

Pouches PPC75-PPC77 show use of different fibers.

Example 3I-I—Pouches

Pouches PPC81-PPC94 containing nicotine premix are prepared comprising powdered compositions as outlined in table 13I and 13II. The pouches are made as follows.

Fibers and powder ingredients (except glidants) are mixed using a Lödige mixer for 2 minutes. Then, Nicotine premix is added and mixed for 2 minutes. With the mixer running, water is then added during a period of 15 minutes followed by liquid flavor (if any—mixed for 15 minutes) and glidant (if any—mixed for 1 minute). The total mixing time is 19-35 minutes.

The final powder composition is filled into pouches (target fill weight 500 mg powder per pouch). The pouch material of example 1A, made from long fiber paper, is used. The powder is filled into pouches and is maintained in the pouch by a sealing. The pouch material of example 1B may also be used.

TABLE 13 I/II

| | PPC 81 | PPC 82 | PPC 83 | PPC 84 | PPC 85 | PPC 86 | PPC 87 | PPC 88 |
|---|---|---|---|---|---|---|---|---|
| Amount of nicotine | 9.6 mg | 9.6 mg | 9.6 mg | 9.6 mg | 9.6 mg | 9.6 mg | 9.6 mg | 9.6 mg |
| Water content [wt %] | 30 | 30 | 30 | 30 | 30 | 30 | 30 | 30 |

TABLE 13 I/II-continued

| | PPC 81 | PPC 82 | PPC 83 | PPC 84 | PPC 85 | PPC 86 | PPC 87 | PPC 88 |
|---|---|---|---|---|---|---|---|---|
| Raw material | Content in weight percent | | | | | | | |
| Nicotine premix II | 14.6 | 14.6 | 14.6 | 14.6 | — | — | — | — |
| Nicotine premix VI | — | — | — | — | 6.4 | 6.4 | 6.4 | 6.4 |
| Purified water | 25 | 25 | 25 | 25 | 28 | 28 | 28 | 28 |
| Wheat fiber | 30 | — | — | — | — | — | — | 15 |
| Oat fiber | — | 30 | — | — | 15 | — | — | — |
| Pea fiber | — | — | 30 | — | — | 15 | — | — |
| Powdered cellulose | — | — | — | 30 | — | — | 15 | — |
| Xylitol DC | 5.0 | 5.0 | 5.0 | 5.0 | 5.0 | 5.0 | 5.0 | 5.0 |
| Erythritol | 8.3 | 8.3 | 8.3 | 8.3 | 28.5 | 28.5 | 28.5 | 28.5 |
| Sodium alginate | 2.0 | 2.0 | 2.0 | 2.0 | 2.0 | 2.0 | 2.0 | 2.0 |
| Sodium carbonate | 5.0 | 5.0 | 5.0 | 5.0 | 5.0 | 5.0 | 5.0 | 5.0 |
| Flavor | 7.0 | 7.0 | 7.0 | 7.0 | 7.0 | 7.0 | 7.0 | 7.0 |
| High intensity sweetener | 1.0 | 1.0 | 1.0 | 1.0 | 1.0 | 1.0 | 1.0 | 1.0 |
| Potassium sorbate | 0.1 | 0.1 | 0.1 | 0.1 | 0.1 | 0.1 | 0.1 | 0.1 |
| Silicon dioxide | 2.0 | 2.0 | 2.0 | 2.0 | 2.0 | 2.0 | 2.0 | 2.0 |
| Total | 100 | 100 | 100 | 100 | 100 | 100 | 100 | 100 |

TABLE 13 II/II

| | PPC 89 | PPC 90 | PPC 91 | PPC 92 | PPC 93 | PPC 94 |
|---|---|---|---|---|---|---|
| Amount of nicotine | 9.6 mg | 9.6 mg | 9.6 mg | 9.6 mg | 96 mg | 9.6 mg |
| Water content [wt %] | 30 | 30 | 30 | 30 | 30 | 30 |
| Raw material | Content in weight percent | | | | | |
| Nicotine premix II | 14.6 | 14.6 | 14.6 | 14.6 | — | — |
| Nicotine premix VI | — | — | — | — | 6.4 | 6.4 |
| Purified water | 25 | 25 | 25 | 25 | 28 | 28 |
| Wheat fiber | 15 | — | — | — | 15 | 15 |
| Oat fiber | — | 15 | — | — | — | — |
| Pea fiber | — | — | 15 | — | — | — |
| Powdered cellulose | — | — | — | 15 | — | — |
| Xylitol DC | 5.0 | 5.0 | 5.0 | 5.0 | 5.0 | 5.0 |
| Erythritol | 23.3 | 23.3 | 23.3 | 23.3 | 28.5 | 20.5 |
| Sodium alginate | 2.0 | 2.0 | 2.0 | 2.0 | | |
| NaCl | — | — | — | — | — | 10 |
| Sodium carbonate | 5.0 | 5.0 | 5.0 | 5.0 | 3.5 | 5.0 |
| Sodium bicarbonate | — | — | — | — | 3.5 | — |
| Flavor | 7.0 | 7.0 | 7.0 | 7.0 | 7.0 | 7.0 |
| High intensity sweetener | 1.0 | 1.0 | 1.0 | 1.0 | 1.0 | 1.0 |

TABLE 13 II/II-continued

| | PPC | | | | | |
|---|---|---|---|---|---|---|
| | PPC 89 | PPC 90 | PPC 91 | PPC 92 | PPC 93 | PPC 94 |
| Potassium sorbate | 0.1 | 0.1 | 0.1 | 0.1 | 0.1 | 0.1 |
| Silicon dioxide | 2.0 | 2.0 | 2.0 | 2.0 | 2.0 | 2.0 |
| Total | 100 | 100 | 100 | 100 | 100 | 100 |

The nicotine premixes comprise water in varying amount, thereby contributing to the total water content.
Pouch content: 500 mg total, i.e. nicotine conc 19.2 mg/g
Wheat fiber, trade name "Vitacel 600 WF plus" or "Vitacel 200WF".
Powdered cellulose, trade name "Vitacel L00" or "Vitacel L700G".
Oat fiber, trade name "Vitacel HF 600".
Pea fiber, trade name "Vitacel EF150".

Other fibers may be used as well, such as water-insoluble plant fibers, such as oat fibers, pea fibers, rice fiber, maize fibers, oat fibers, tomato fibers, barley fibers, rye fibers, sugar beet fibers, buckwheat fibers, potato fibers, powdered cellulose, cellulose fibers, apple fibers, cocoa fibers, bamboo fibers, bran fibers, and cellulose fiber.

For example, a mixture of e.g. menthol and peppermint may be used. Of course, other flavors as described herein may be use as well, in combination with menthol and/or peppermint or replacing these.

Silicon dioxide is used as a glidant. Other possible glidants include e.g. magnesium stearate, starch and talc.

Sodium alginate, glycerol and hydroxypropyl cellulose (HPC) may be used as humectants. Other humectants as described herein may also be used in combination with sodium alginate, glycerol or HPC or as an alternative.

Sodium carbonate and sodium bicarbonate are used as alkaline buffering agent. Other buffering agents as described herein may also be used in combination with sodium carbonate or an alternative.

Potassium sorbate is used as a preservative. Other preservatives as described herein may be used in combination with or instead of potassium sorbate.

Acesulfame potassium and/or sucralose may as an example be used as high intensity sweeteners. Other usable high intensity sweeteners described herein may be used in combination with or instead of acesulfame potassium and/or sucralose.

Pouches PPC81-PPC92 shows the use of different fibers, in different amounts and with different nicotine premixes.

Pouches PPC93-PPC94 show use of buffer pair and higher amount of salt, respectively.

Example 3I-II Pouches

Pouches PPC111-PPC117 containing nicotine premix are prepared comprising powdered compositions as outlined in table 13III. The pouches are made as follows.

Powdered ingredients including powdered flavor (if any) are mixed using a planetary Bear Varimixer mixer for 2 minutes. Then, the nicotine is added and mixed for 2 minutes. Then water is slowly added while the mixer is running, followed by addition of liquid flavor. Finally, silicon dioxide is added and the mixed for about 1 minute. The total mixing time is about 30 minutes.

The final powder composition is filled into pouches (target fill weight 500 mg powder per pouch). The pouch material of example 1, made from long fiber paper, is used. The powder is filled into pouches and is maintained in the pouch by a sealing.

The material of the pouches is heat sealable non-woven cellulose, such as long fiber paper. Pouches that are not in form of non-woven cellulose fabric may also be used according to the invention.

The powder is filled into pouches and is maintained in the pouch by a sealing.

TABLE 13III

| | PPC | | | | | | |
|---|---|---|---|---|---|---|---|
| | PPC 111 | PPC 112 | PPC 113 | PPC 114 | PPC 115 | PPC 116 | PPC 117 |
| Amount of nicotine | 9.6 mg | 9.6 mg | 9.6 mg | 9.6 mg | 9.6 mg | 9.6 mg | 9.6 mg |
| Water content [wt %] | 15 | 45 | 30 | 30 | 30 | 30 | 30 |
| Density (gram per Liter) | 256 | 303 | 578 | ND | ND | ND | ND |
| Hausner ratio | 1.25 | 1.22 | 1.11 | ND | ND | ND | ND |
| Raw material | Content in weight percent | | | | | | |
| Nicotine premix II | 14.6 | 14.6 | 14.6 | 14.6 | 14.6 | 14.6 | 14.6 |
| Sugar alcohol(s) | 12.3 | 12.3 | 12.3 | 12.4 | 12.7 | 12.1 | 11.9 |
| Purified water | 10 | 25 | 40 | 25 | 25 | 25 | 25 |
| Wheat fiber | 45 | 30 | 15 | 30 | 30 | 30 | 30 |
| Sodium alginate | 2.0 | 2.0 | 2.0 | 2.0 | 2.0 | 2.0 | 2.0 |
| Sodium carbonate | 4.0 | 4.0 | 4.0 | 4.0 | 4.0 | 4.0 | 4.0 |
| Flavor | 9.0 | 9.0 | 9.0 | 9.0 | 9.0 | 9.0 | 9.0 |
| High intensity sweetener | 1.0 | 1.0 | 1.0 | 1.0 | 1.0 | 1.0 | 1.0 |
| Potassium sorbate | 0.1 | 0.1 | 0.1 | 0.01 | 0.05 | 0.2 | 0.5 |
| Silicon dioxide | 2.0 | 2.0 | 2.0 | 2.0 | 2.0 | 2.0 | 2.0 |
| Total | 100 | 100 | 100 | 100 | 100 | 100 | 100 |

The nicotine premix II comprises 34.1 wt % water, thereby contributing to the total water content.
Pouch content: 500 mg total, i.e. nicotine concentration 19.2 mg/g
The sugar alcohol(s) may be Xylitol e.g. trade name "Xylitab 200" and/or Isomalt e.g. tradename "GalenIQ 720".

Wheat fiber, trade name "Vitacel 600 WF plus". Other fibers may be used as well, such as water-insoluble plant fibers, such as oat fibers, pea fibers, rice fiber, maize fibers, oat fibers, tomato fibers, barley fibers, rye fibers, sugar beet fibers, buckwheat fibers, potato fibers, cellulose fibers, bran fibers, bamboo fibers, powdered cellulose, apple fibers, cocoa fibers, and cellulose fiber.

For example, a mixture of e.g. menthol and peppermint may be used. Of course, other flavors as described herein may be use as well, in combination with menthol and/or peppermint or replacing these.

Sodium alginate, glycerol and hydroxypropyl cellulose (HPC) may be used as humectants. Other humectants as described herein may also be used in combination with sodium alginate, glycerol or HPC or as an alternative.

Silicon dioxide is used as a glidant. Other possible glidants include e.g. magnesium stearate, starch and talc.

Sodium carbonate is used as an alkaline buffering agent. Other buffering agents as described herein may also be used in combination with sodium carbonate or an alternative.

Potassium sorbate is used as a preservative. Other preservatives as described herein may be used in combination with or instead of potassium sorbate.

Acesulfame potassium may as an example be used as high intensity sweeteners. Other usable high intensity sweeteners described herein may be used in combination with or instead of acesulfame potassium.

Pouches PPC111-PPC113 show pouches having different water and water-insoluble fiber contents.

PPC114-117 show varying amount of preservative.

Example 3J Content Uniformity Measurements

Content Uniformity (CU) of a pouch sample was determined by analysis of 10 replicate sub-samples. For each sub-sample of approx. 500 mg, the content of nicotine was determined using standard HPLC techniques. The nicotine content of a sub-sample was expressed as a percentage relative to the nominal content of nicotine in the sample (ie. % Label Claim). For example, a pouch sample with a nominal content of nicotine of 20 mg/g being analyzed to have an actual content of 19 mg/g would have a nicotine content of 95% Label Claim.

The Content Uniformity of the sample is then determined as the Relative Standard Deviation (RSD) of the individual analyses of relative nicotine content in the 10 replicates.

Example 3K—Release Test (In Vivo)

The release properties of the pouches were evaluated by a panel of assessors, preferably at least 8 assessors. Each assessor was provided with a pouch to place in the oral cavity, specifically at the upper lip.

Pouch was removed from the oral cavity of the test person after 2 min., 5 min., 10 min., 30 min. or 60 min.

The amount of remaining nicotine in the pouches were determined using standard HPLC techniques.

Two pouches were tested for each timepoint. The average of the result obtained for each timepoint was used to make profiles of the nicotine content in the pouches over time.

The amount of released nicotine could thereafter be obtained by subtracting the remaining amount of nicotine in the pouch from the initial dosage of nicotine in the tested pouch.

Example 3L—Release Test (In Vitro)

The release properties of the pouches were tested in an in vitro experiment.

Individual pouches were put into reaction tubes having a diameter of approx. 2 cm and containing 10 mL of 0.02 M potassium dihydrogen phosphate-buffer (pH adjusted to 7.4) at warmed to 37 degrees Celsius.

No stirring or shaken was applied during the release experiment.

Pouches were removed from the buffer after 2 min., 5 min., 10 min., 30 min. or 60 min. Excess buffer was removed, and the amount of remaining nicotine were determined using standard HPLC.

Two pouches were tested for each timepoint. The average of the result obtained for each timepoint was used to make profiles of the nicotine content in the pouches over time.

The amount of released nicotine could thereafter be obtained by subtracting the remaining amount of nicotine in the pouch from the initial dosage of nicotine in the tested pouch.

Example 3M—Release Results

Pouches were exposed to the in vitro release experiment described in example 3L.

TABLE 14

| PPC | Fiber | Remaining nicotine in pouch after 2 min | Remaining nicotine in pouch after 10 min | Release rate in time period: 2-10 min (% per min.) |
|---|---|---|---|---|
| PPC82 | Oat (HF600) | 74.7% | 67.9% | 0.85 |
| PPC81 | Wheat (WF600) | 80.0% | 71.6% | 1.05 |
| PPC84 | Cellulose L00 | 66.6% | 62% | 0.58 |
| PPC83 | Pea fiber | 78% | 62.0% | 2.00 |
| PPC81 | Wheat (WF200) | 85.2% | 63.6% | 2.70 |
| PPC89 | Wheat (WF200) | ND | 64.5% | ND |
| PPC92 | Cellulose L00 | ND | 64.6% | ND |
| PPC91 | Pea fiber | ND | 64.5% | ND |
| PPC84 | Cellulose L700G | ND | 47.3% | ND |
| PPC89 | Wheat (WF600) | 79% | 72% | 0.88 |

ND = not determined.

The release results show an increased release of nicotine after 10 min for pouches comprising fibers with a relative high water binding capacity, such as pea fibers, cellulose L700G and wheat fibers (WF200).

Example 3N—Release Results

Pouches with pouch compositions similar to PPC46 were made, however, using the below indicated humectant, were exposed to the in vitro release experiment described in example 3L.

TABLE 15

| Different humectants. | |
|---|---|
| Humectant | Remaining nicotine in pouch after 10 min |
| Modified starch | 68% |
| Glycerol | 71% |
| Alginate (PPC46) | 79% |

Example 3O—Release Results

Pouches were exposed to the in vitro release experiment described in example 3L.

TABLE 16

| Release results. | | | |
|---|---|---|---|
| PPC | Weight % Fiber | Nicotine premix | Remaining nicotine in pouch after 10 min |
| PPC81 | 30 wt % Wheat (WF600) | II | 71.6% |
| PPC61 | 30 wt % Wheat (WF600) | VI | 66.6% |

TABLE 16-continued

Release results.

| PPC | Weight % Fiber | Nicotine premix | Remaining nicotine in pouch after 10 min |
|---|---|---|---|
| PPC88 | 15 wt % Wheat (WF600) | VI | 43.6% |
| PPC89 | 15 wt % Wheat (WF600) | II | 54.4% |
| PPC93 | 15 wt % Wheat (WF600) | VI | 34.6% |
| PPC94 | 15 wt % Wheat (WF600) | VI | 43.7% |
| PPC76 | 30 wt % peafiber | VI | 58.2% |
| PPC83 | 30 wt % peafiber | II | 62.0% |

ND = not determined.

Results demonstrate that release after 10 min is improved when using nicotine premix VI. The release can be further improved by including a buffer system, i.e. 3.5% sodium carbonate and 3.5% sodium bicarbonate (PPC93).

Also, the addition of 10% NaCl seems to improve the release obtained after 10 min (PPC94).

Example 4—Evaluation

The produced pouches of the invention were evaluated and found highly suitable as delivery vehicles of nicotine in that they provide a favorable release of nicotine and at the same time are pleasant to the user, e.g. with respect to a desirable sticky texture. In particular, the pouches of the invention did not need any wetting before use as opposed to conventional nicotine pouches with low moisture content which may feel dry initially in use.

The pouch product PPC1 was compared to the Comp. NPR pouch with respect to perceived effect from nicotine and with respect to burning (tingling) sensation.

Evaluation of perceived effect from nicotine and burning (tingling) sensation is performed as described in the following.

Perceived effect from nicotine and burning (tingling) sensation was evaluated by a test panel of 4 trained assessors. Each assessor evaluates all samples twice. Average evaluations are estimated.

The pouch product PPC1 was evaluated to have a faster onset of action and a higher perceived effect from nicotine by all four assessors, when comparing to the Comp. NPR pouch. Also, all four assessors evaluated the pouch product PPC1 to have a higher burning (tingling) sensation compared to the Comp. NPR pouch.

Similarly, the pouch product PPC1 was compared to the Comp. NBT pouch with respect to perceived effect from nicotine in the same way as described above. The pouch product PPC1 was evaluated to have a higher perceived effect from nicotine by all four assessors compared to the Comp. NBT pouch.

What is claimed:

1. A nicotine pouch composition comprising a free-base nicotine mixture, said pouch composition having a water content of at least 15% by weight of said pouch composition, wherein the free-base nicotine mixture comprises at least one selected from the group consisting of free-base nicotine mixed with ion exchange resin, free-base nicotine mixed with a water-soluble fiber, and combinations thereof.

2. The nicotine pouch composition according to claim 1, wherein the pouch composition comprises sugar alcohol.

3. The nicotine pouch composition according to claim 2, wherein said sugar alcohol is selected from the group consisting of sorbitol, erythritol, xylitol, maltitol, mannitol, hydrogenated starch hydrolyzates, isomalt, and any combination thereof.

4. The nicotine pouch composition according to claim 2, wherein the pouch composition comprises sugar alcohol in an amount of 5%-70% by weight of the pouch composition.

5. The nicotine pouch composition according to claim 1, wherein the pouch composition further comprises a pH-regulating agent.

6. The nicotine pouch composition according to claim 5, wherein the pouch composition comprises pH-regulating agent in an amount of between 0.01 and 15% by weight of the pouch composition.

7. The nicotine pouch composition according to claim 5, wherein the pH regulating agent is a basic pH regulating agent.

8. The nicotine pouch composition according to claim 5, wherein the pH regulating agent is selected from the group consisting of Sodium carbonate, Sodium bicarbonate, Potassium carbonate, Potassium bicarbonate, Magnesium carbonate, and combinations thereof.

9. The nicotine pouch composition according to claim 5, wherein the nicotine pouch composition comprises an acidic pH regulating agent.

10. The nicotine pouch composition according to claim 9, wherein the nicotine pouch composition further comprises an alkaline pH regulating agent and wherein the pouch composition is adapted to give a pH of at least 8.0.

11. The nicotine pouch composition according to claim 9, wherein the acidic pH regulating agent is selected from the group consisting of Acetic acid; Adipic acid, Citric acid, Fumaric acid, Glucono-6-lactone, Gluconic acid, Lactic acid, Malic acid, Maleic acid, Tartaric acid, Succinic acid, Propionic acid, Ascorbic acid, Phosphoric acid, Carbonic acid, Benzoic acid, and salts thereof.

12. The nicotine pouch composition according to claim 1, wherein the pouch composition further comprises a humectant.

13. The nicotine pouch composition according to claim 1, wherein the pouch composition is free of silicon dioxide.

14. The nicotine pouch composition according to claim 1, wherein the pouch composition further comprises a water-insoluble composition in an amount of between 5% and 50% by weight of the pouch composition.

15. The nicotine pouch composition according to claim 1, wherein the pouch composition further comprises an amount of a water-insoluble composition, wherein the water-insoluble composition comprises or consists of water-insoluble fiber.

16. The nicotine pouch composition according to claim 15, wherein the water-insoluble fiber is selected from the group consisting of wheat fibers, oat fibers, pea fibers, rice fiber, maize fibers, tomato fibers, barley fibers, lye fibers, sugar beet fibers, buckwheat fibers, potato fibers, cellulose fibers, apple fibers, cocoa fibers, cellulose fiber, powdered cellulose, bamboo fibers, bran fibers and combinations thereof.

17. The nicotine pouch composition according to claim 15, wherein e water-insoluble fiber comprises microcrystalline cellulose.

18. The nicotine pouch composition according to claim 15, wherein the water-insoluble fiber comprises powdered cellulose.

19. The nicotine pouch composition according to claim 15, wherein the water-insoluble fiber comprises at least two different types of fibers.

20. The nicotine pouch composition according to claim 19, wherein the water-insoluble fiber comprises powdered cellulose.

21. The nicotine pouch composition according to claim 1, wherein the pouch composition has a water content of 15 to 70% by weight of said pouch composition.

22. The nicotine pouch composition according to claim 1, wherein the pouch composition comprises nicotine in an amount corresponding to 0.5 to 20 mg per pouch.

23. The nicotine pouch composition according to claim 1, wherein the pouch composition is free of tobacco, tobacco fibers and fibers derived from tobacco.

24. The nicotine pouch composition according to claim 1, wherein the composition comprises flavor.

25. The nicotine pouch composition according to claim 1, wherein the water-soluble fiber is selected from inulin, polydextrose, dextrin, maltodextrin, and mixtures thereof.

26. The nicotine pouch composition according to claim 25, wherein the polydextrose is refined polydextrose.

27. An oral nicotine pouch product comprising a pouch and an amount of the nicotine pouch composition according to claim 1 enclosed in said pouch.

28. The oral nicotine pouch product according to claim 27, wherein the pouch composition is a non-tobacco pouch composition,
wherein the nicotine pouch composition comprises sugar alcohol in an amount of 10-60% by weight of the pouch composition, said sugar alcohol being selected from the group consisting of sorbitol, erythritol, xylitol, lactitol, maltitol, mannitol, hydrogenated starch hydrolyzates, isomalt, and combinations thereof,
wherein the pouch composition comprises pH regulating agent in an amount of 0.01% and 15% by weight of the pouch composition, and
wherein the pouch composition comprises water-insoluble fiber in an amount of 10%-50% by weight of the pouch composition.

29. A nicotine pouch composition comprising free-base nicotine and water-soluble fiber, said pouch composition having a water content of at least 15% by weight of said pouch composition.

* * * * *